US010481150B2

(12) United States Patent
Simmons et al.

(10) Patent No.: US 10,481,150 B2
(45) Date of Patent: Nov. 19, 2019

(54) MICROFLUIDIC DEVICE FOR CELL-BASED ASSAYS

(71) Applicant: THE GOVERNING COUNCIL OF THE UNIVERSITY OF TORONTO, Toronto (CA)

(72) Inventors: Craig Simmons, Toronto (CA); Oleg Chebotarev, Toronto (CA)

(73) Assignee: THE GOVERNING COUNCIL OF THE UNIVERSITY OF TORONTO, Toronto (CA)

( * ) Notice: Subject to any disclaimer, the term of this patent is extended or adjusted under 35 U.S.C. 154(b) by 27 days.

(21) Appl. No.: 15/521,744

(22) PCT Filed: Oct. 27, 2015

(86) PCT No.: PCT/CA2015/051095
§ 371 (c)(1),
(2) Date: Apr. 25, 2017

(87) PCT Pub. No.: WO2016/065470
PCT Pub. Date: May 6, 2016

(65) Prior Publication Data
US 2017/0248583 A1 Aug. 31, 2017

Related U.S. Application Data

(60) Provisional application No. 62/068,859, filed on Oct. 27, 2014.

(51) Int. Cl.
*G01N 1/00* (2006.01)
*G01N 33/50* (2006.01)
(Continued)

(52) U.S. Cl.
CPC ........ *G01N 33/5088* (2013.01); *B01L 3/5027* (2013.01); *B01L 3/5085* (2013.01);
(Continued)

(58) Field of Classification Search
CPC ....................................................... G01N 1/00
See application file for complete search history.

(56) References Cited

U.S. PATENT DOCUMENTS 6,338,802 B1 * 1/2002 Bodner ................. B01D 61/18
210/261
6,780,584 B1 * 8/2004 Edman ................. B01J 19/0046
422/50

(Continued)

FOREIGN PATENT DOCUMENTS

CA       2617606 A1    2/2007
WO    2009088993 A2    7/2009
(Continued)

OTHER PUBLICATIONS

Chen, et al., A 3D Microfluidic Platform Incorporating Methacrylated Gelatin Hydrogels to Study Physiological Cardiovascular Cell-Cell Interactions, Lab on a Chip, 2013, 13:2591-2598.
(Continued)

Primary Examiner — Jyoti Nagpaul
(74) Attorney, Agent, or Firm — Quarles & Brady LLP

(57) ABSTRACT

A microfluidic device, method and kit for assaying and/or culturing cells are provided. The microfluidic device comprises a well block comprising a plurality of microwells; at least one cell culture layer selected from a first cell culture layer comprising a plurality of microchannels, each microchannel being aligned with one of the plurality of microwells and being in fluid communication with the aligned microwells; and a second cell culture layer comprising a plurality of cell culture chamber wells, each cell culture chamber well being aligned with one of the plurality of microwells and being in fluid communication with the aligned microwells, and a plurality of outlets, each of the plurality of outlets corresponding to one of the plurality of cell culture chamber wells; and a base block, wherein the at
(Continued)

least one cell culture layer is sealably coupled between the well block and the base block, thereby allowing fluid communication between the plurality of microwells in the well block and the at least one cell culture layer.

18 Claims, 38 Drawing Sheets

(51) Int. Cl.
*C12M 3/06* (2006.01)
*C12N 5/00* (2006.01)
*B01L 3/00* (2006.01)
*C12M 1/32* (2006.01)
*C12M 1/00* (2006.01)
*C12M 1/12* (2006.01)

(52) U.S. Cl.
CPC ............ *C12M 23/12* (2013.01); *C12M 23/16* (2013.01); *C12M 23/40* (2013.01); *C12M 25/02* (2013.01); *C12M 29/10* (2013.01); *C12N 5/0075* (2013.01); *G01N 33/5058* (2013.01); *G01N 33/5067* (2013.01); *B01L 2200/0689* (2013.01); *B01L 2300/0645* (2013.01); *B01L 2300/0681* (2013.01); *B01L 2300/0829* (2013.01); *B01L 2400/049* (2013.01); *G01N 2500/10* (2013.01)

(56) References Cited

U.S. PATENT DOCUMENTS

| 8,257,964 | B2 | 9/2012 | Hung et al. |
| 2013/0090268 | A1 | 4/2013 | Hung et al. |

FOREIGN PATENT DOCUMENTS

| WO | 2010009307 A2 | 1/2010 |
| WO | 2011014674 A2 | 2/2011 |
| WO | 2012118799 A2 | 9/2012 |
| WO | 2013086329 A1 | 6/2013 |
| WO | 2013086502 A1 | 6/2013 |
| WO | 2013148745 A1 | 10/2013 |

OTHER PUBLICATIONS

Conant, et al., Well Plate Microfluidic System for Investigation of Dynamic Platelet Behavior Under Variable Shear Loads, Biotechnology and Bioengineering, 2011, 108(12):2978-2987.
Meyvantsson, et al., Automated Cell Culture in High Density Tubeless Microfluidic Device Arrays, Lab on a Chip, 2008, 8:717-724.
Srigunapalan, et al., A Microfluidic Membrane Device to Mimic Critical Components of the Vascular Microenvironment, Biomicrofluidics, 2011, 5:013409-1-013409-9.
Young, et al., Matrix-Dependent Adhesion of Vascular and Valvular Endothelial Cells in Microfluidic Channels, Lab on a Chip, 2007, 7:1759-1766.
Young, et al., Technique for Real-Time Measurements of Endothelial Permeability in a Microfluidic Membrane Chip Using Laser-Induced Fluorescence Detection, Analytical Chemistry, 2010, 82(3):808-816.
PCT International Search Report, PCT/CA2015/051095, dated Feb. 8, 2016.
PCT Written Opinion of the International Searching Authority, PCT/CA2015/051095, dated Feb. 8, 2016.
European Patent Office, Extended European Search Report, Application No. 15855382.6, Jun. 4, 2018, 12 pages.

\* cited by examiner

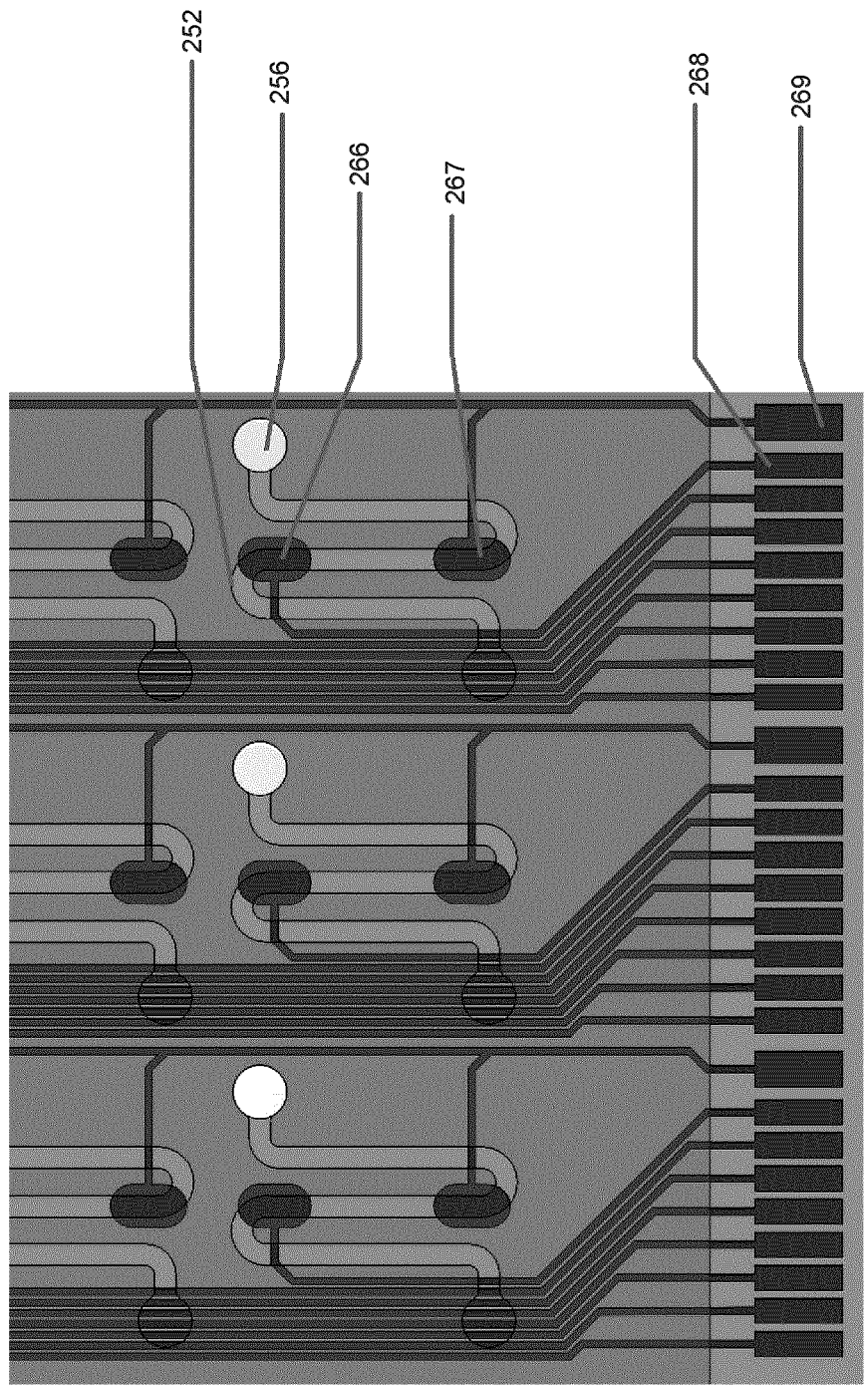

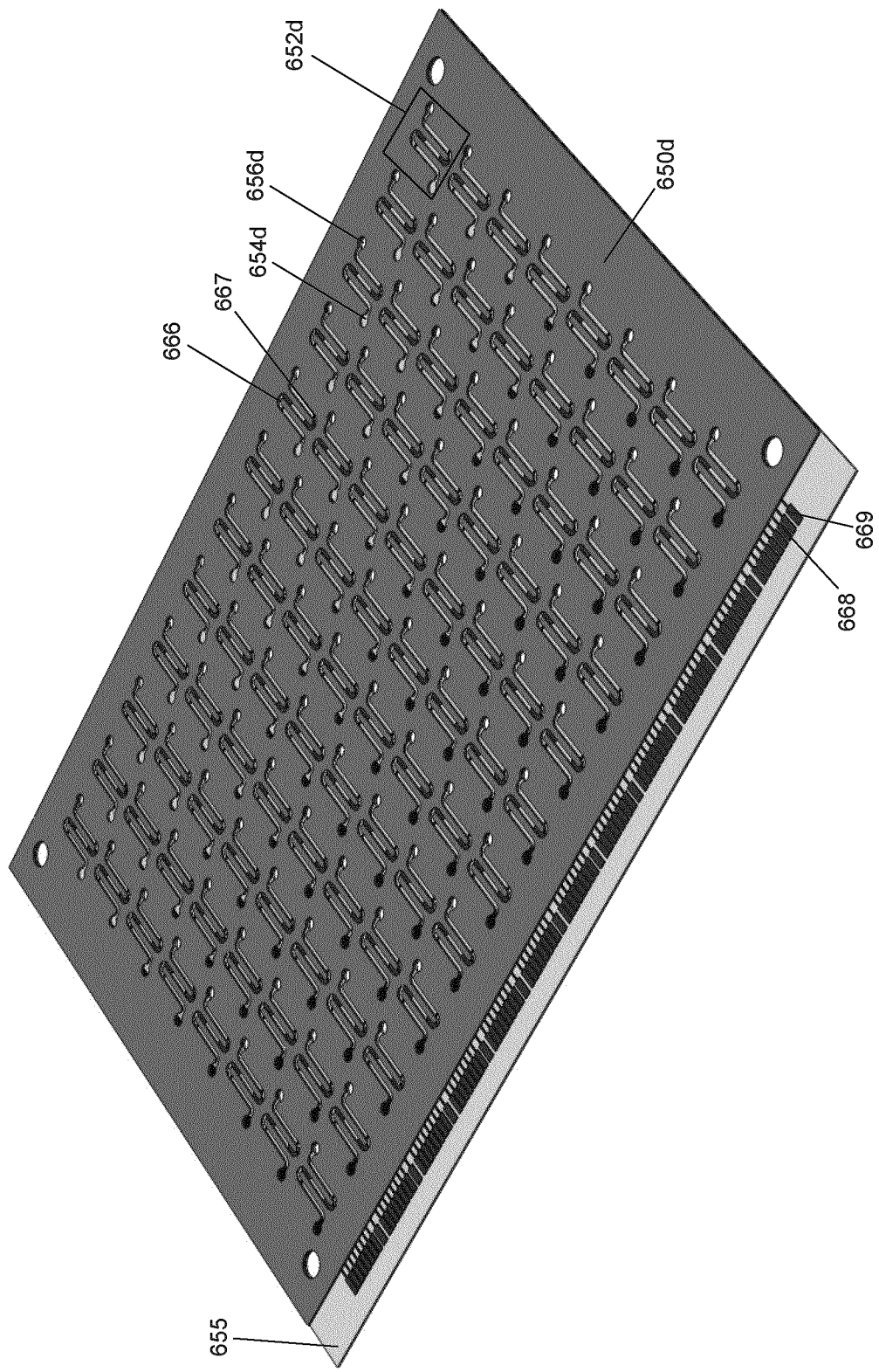

MICROFLUIDIC DEVICE FOR CELL-BASED ASSAYS

CROSS-REFERENCE TO RELATED APPLICATIONS

This application represents the national stage entry of PCT International Application No. PCT/CA2015/051095 filed on Oct. 27, 2015, which claims priority to US Provisional Patent Application 62/068,859, filed Oct. 27, 2014, all of which are incorporated herein by reference as if set forth in their entirety.

FIELD OF THE DESCRIPTION

The present description relates generally to microfluidic devices for cell culture and cell-based assays. More specifically, the present description relates to a microfluidic device for use in medium- to high-throughput cell-based assays, the device being adapted for use with standard liquid handling systems and plate reader systems.

BACKGROUND OF THE DESCRIPTION

Microfluidic technology has attracted interest for biotechnology and pharmaceutical applications, including drug screening and toxicology testing. Microfluidics refers to the design of systems in which small volumes (e.g., µL, nL, pL or fL) of fluids are moved or otherwise handled. For example, one or more microfluidic channels or network of channels may be used to direct flow of fluids in a device, wherein cellular, chemical or molecular processes or reactions take place in the channels by virtue of the fluidic properties of the channels. The term "microfluidic" typically refers to fluids provided to channels having internal dimensions of between about 0.1 and 500 µm.

Microfluidic platforms have been studied for use in vascular applications at least in part because they can be configured to facilitate predictable flow characteristics and physiologically relevant dimensions. For example, single channel microfluidic devices have been used to examine endothelial cell adhesion (Young et al. Lab on a Chip 2007; 7:1759-1766) and endothelial drug permeability (Young et al. Analytical Chemistry 2010; 82:808-816), and to demonstrate monocyte adhesion and transmigration through endothelium (Srigunapalan et al. Biomicrofluidics 2011; 5:13409). Flow-regulated paracrine interactions between an endothelial monolayer and myofibroblasts embedded in a 3D "microtissue" hydrogel have also been examined in a single microchannel platform (Chen et al. Lab on a Chip 2013; 13:2591-8). However, single microchannel platforms are not suitable for many biotechnology and pharmaceutical applications, which require medium- to high-throughput capacity.

Microfluidic platforms configured for medium- to high-throughput use are known. For example, devices described in PCT/US2009/00045, PCT/US2010/043743 and Meyvantsson et al. (Lab on a Chip 2008; 8:717-724) were designed for used in cell-based flow assays. However, these devices use passive flow mechanisms (e.g., capillary or gravity driven flow), which do not mimic physiological flow forces, such as those in blood vessels. The 24-well BioFlux system (Conant et al. *Biotechnol Bioeng* 2011; 108:2978-87) has been used to study the effects of flow on a monolayer of endothelial cells in two dimensions. However, the BioFlux system requires complex and proprietary machinery and vast networks of tubing that are incompatible with standard robotic liquid handling systems and standard microplate readers, hindering their use for medium- to high-throughput drug and toxicology screening. Further, none of the aforementioned medium- to high-throughput devices mimic three-dimensional vascularized tissues, which facilitate interaction of multiple cell types interacting in a physiologically relevant manner.

Co-culture microfluidic devices capable of mimicking 3D physiological environments, sometimes referred to as "organ-on-a-chip" are known (e.g., PCT/US2009/050830, PCT/US2012/068766, and PCT/US2012/068461), but none of these platforms provides a level of throughput or compatibility with standard liquid handling and plate reading systems that are desirable in many biotechnology and pharmaceutical applications.

It is desirable to obviate or mitigate one or more of the above deficiencies.

SUMMARY OF THE DESCRIPTION

In a first aspect, a microfluidic device for assaying cells is provided. The microfluidic device comprises: a well block comprising a plurality of microwells; a first cell culture layer comprising a plurality of microchannels, each microchannel being aligned with one of the plurality of microwells and being in fluid communication with the aligned microwells; and a base block, the base block being in fluid communication with the plurality of microchannels, wherein the first cell culture layer is sealably coupled between the well block and the base block, thereby allowing fluid communication between the plurality of microwells in the well block, the aligned microchannels in the first cell culture layer and the base block.

In one embodiment of the first aspect, the plurality of microchannels have defined geometries that produce one or more desired flow rates through the plurality of microchannels.

In one embodiment of the first aspect, an internal bottom surface of each of the plurality of microchannels comprises a material that is compatible with cell adherence and/or growth. In one embodiment of the first aspect, the internal bottom surface is integral with the first cell culture layer. In one embodiment of the first aspect, the internal bottom surface comprises a porous or semi-porous membrane that is coupled to the first cell culture layer. In one embodiment of the first aspect, the porous or semi-porous membrane comprises electrodes.

In one embodiment of the first aspect, the device further comprises a second cell culture layer comprising a plurality of cell culture chamber wells and corresponding outlets, each cell culture chamber well being aligned with one of the plurality of microchannels and being in fluid communication with the aligned microchannels, each corresponding outlet being in fluid communication with the aligned microchannels and the base block. In one embodiment, the second cell culture layer is sealably coupled between the first cell culture layer and the base block, thereby allowing fluid communication between each of the plurality of microwells in the well block, the aligned microchannels in the first cell culture layer, the second cell culture layer and the base block.

In one embodiment of the first aspect, the device further comprises a non-permeable layer disposed between the plurality of cell culture chamber wells and the first cell culture layer, the non-permeable layer for preventing fluid flow in the plurality of cell culture chamber wells.

In one embodiment of the first aspect, the device further comprises a fluid collection layer comprising a plurality of fluid collection chambers, each fluid collection chamber being aligned with and in fluid communication with one of the plurality of microwells and one of the plurality of microchannels, wherein the fluid collection layer is sealably coupled between the well block and the base block.

In one embodiment of the first aspect, the base block comprises an outlet configured to be coupled to a flow or vacuum manifold.

In a second aspect, a microfluidic device for assaying cells is provided. The microfluidic device comprises: a well block comprising a plurality of microwells; a cell culture layer comprising a plurality of cell culture chamber wells, each cell culture chamber well being aligned with one of the plurality of microwells and being in fluid communication with the aligned microwells, and a plurality of outlets, each of the plurality of outlets corresponding to one of the plurality of cell culture chamber wells; and a base block, wherein the cell culture layer is sealably coupled between the well block and the base block.

In one embodiment of the second aspect, the device further comprises one or more seals for preventing fluid communication between the plurality of outlets of the cell culture layer and the base block.

In one embodiment of the second aspect, the device further comprises a second cell culture layer comprising a plurality of microchannels, each microchannel being aligned with one of the plurality of microwells and one of the plurality of cell culture chamber wells, each microchannel being in fluid communication with the aligned microwells, the aligned cell culture chamber wells and corresponding outlet. In one embodiment, the second cell culture layer is sealably coupled between the well block and the first cell culture layer, thereby allowing fluid communication between each of the plurality of microwells in the well block, the aligned microchannels in the second cell culture layer and the first cell culture layer.

In one embodiment of the second aspect, the base block is configured to allow optical access to the plurality of cell culture chamber wells. In one embodiment, the base block is configured to allow optical access to the plurality of microchannels. In one embodiment, the well block has a shape and configuration of a standard well plate.

In a third aspect, a method for culturing and/or assaying cells is provided. The method comprises the steps of: providing one embodiment of the microfluidic device provided herein; providing first cells to be cultured in one or more of the plurality of microchannels; and culturing and/or assaying the first cells provided in the microchannels, wherein the culturing and/or assaying comprises flowing a liquid through the microfluidic device.

In one embodiment of the third aspect, the method further comprises the steps of: providing second cells to be cultured in one or more of the plurality of cell culture chambers wells; and culturing and/or assaying the second cells provided in the cell culture chamber wells, wherein the culturing and/or assaying of the second cells comprises flowing a liquid through the microfluidic device.

In a fourth aspect, a method for imaging and culturing and/or assaying cells is provided. The method comprises the steps of: providing one embodiment of the microfluidic device provided herein; providing first cells to be cultured in one or more of the plurality of cell culture chamber wells; culturing and/or assaying the first cells provided in the cell culture chamber wells, wherein the culturing and/or assaying comprises providing a liquid to the microfluidic device; and imaging the first cells cultured and/or assayed in the cell culture chamber wells, wherein the imaging comprises obtaining an image of the cultured and/or assayed first cells from below the base block.

In one embodiment of the fourth aspect, the method further comprises the steps of: providing second cells to be cultured in one or more of the plurality of microchannels; culturing and/or assaying the second cells provided in the microchannels, wherein the culturing and/or assaying comprises providing a liquid to the microfluidic device; and imaging the second cells cultured and/or assayed in the microchannels, wherein the imaging comprises obtaining an image of the cultured and/or assayed second cells from below the base block.

In a fifth aspect, a kit for assembling a microfluidic device for assaying cells is provided. The kit comprises: at least one well block comprising a plurality of microwells; at least one cell culture layer, the at least one cell culture layer comprising: a plurality of microchannels, each microchannel being alignable with one of the plurality of microwells and being configured for fluid communication with the alignable microwells; or a plurality of cell culture chamber wells, each cell culture chamber well being alignable with one of the plurality of microwells and being configured for fluid communication with the alignable microwells, and a plurality of outlets, each of the plurality of outlets corresponding to one of the plurality of cell culture chamber wells; at least one base block for providing a base for the device; and at least two seals for forming a seal between the well block and the at least one cell culture layer and the at least one cell culture layer and the base block, wherein upon assembly the at least one cell culture layer may be sealably coupled between the well block and the base block, thereby allowing fluid communication between each of the plurality of microwells in the well block and the at least one cell culture layer.

In one embodiment of the fifth aspect, each of the plurality of microchannels comprises an internal bottom surface integral with the first cell culture layer, the internal bottom surface being suitable for culturing cells thereon. In one embodiment, each of the plurality of microchannels comprises an internal bottom surface comprising a porous or semi-porous membrane that is coupled to the first cell culture layer, the porous or semi-porous membrane being suitable for culturing cells thereon. In one embodiment, the porous or semi-porous membrane comprises electrodes.

In one embodiment of the fifth aspect, the base block is configured for fluid communication with the at least one cell culture layer.

In one embodiment of the fifth aspect, the at least one well block is one or more of a deep well block, wherein the plurality of microwells have a liquid capacity of about 1.5 mL, a shallow well block, wherein the plurality of microwells have a liquid capacity of about 0.25 mL, or a pool well block comprising a tray having a liquid capacity of about 150 mL, the tray being disposed above and in fluid communication with the plurality of microwells.

In one embodiment of the fifth aspect, the at least one cell culture layer comprises at least two cell culture layers.

In one embodiment of the fifth aspect, the at least one base block is one or more of: a base block configured for fluid communication with the cell culture layer and comprises an outlet configured for fluid communication with a flow or vacuum manifold; and a base block configured to configured to allow optical access to the at least one cell culture layer.

In one embodiment of the fifth aspect, the kit further comprises: a fluid collection layer comprising a plurality of fluid collection chambers, each fluid collection chamber being configured for alignment and fluid communication with one of the microwells and one of the microchannels when the well block, first cell culture layer and fluid collection layers are aligned and coupled.

In one embodiment of the fifth aspect, the kit further comprises instructions for one or more of: assembling, using or sterilizing the microfluidic device.

BRIEF DESCRIPTION OF THE DRAWINGS

The features of the invention will become more apparent in the following detailed description in which reference is made to the appended drawings wherein:

FIG. 1a depicts an exploded perspective view of the device, wherein the device has four layers.

FIG. 1b depicts an expanded exploded perspective view of one of a plurality of microchannels in a flow chamber of a flow cell culture layer.

FIG. 1c depicts an expanded exploded perspective view of the flow chamber of FIG. 1b, wherein cells have been seeded on the bottom surface inside of a microchannel.

FIG. 1d is a cross-sectional side view of one well of an assembled device of the device of FIG. 1 (base block not shown), wherein the well comprises media (blue liquid), reagents (green diamonds) and suspended cells (red circles) and a cell layer (pink rectangles) on the bottom internal surface of the microchannel in the flow chamber; the arrows indicate directional flow of liquid from the well block through the flow chamber and the outlet of the flow chamber.

FIGS. 2a-k depict various embodiments of a microfluidic device provided herein, wherein the device is configured for use in a three dimensional (i.e., 3D) flow assay or cell culture system.

FIG. 2a depicts an exploded perspective view of the device, wherein the device has five layers.

FIG. 2b depicts an expanded exploded perspective view of one of a plurality of porous flow chambers (upper left), an exploded perspective view of one of a plurality of cell culture chamber wells and corresponding outlets in the static cell culture chamber well (lower left) and a cross-sectional side view of the porous flow chamber (right upper) and the static chamber (right lower).

FIG. 2c (left) depicts a cross-sectional side view of one well and corresponding chambers of an assembled device of the device of FIG. 2, wherein the well comprises media (blue liquid), reagents (green diamonds) and suspended cells (red circles) and a cell layer (pink rectangles) on the porous membrane portion of the porous flow chamber; the arrows indicate directional flow of liquid from the well block through the flow chamber (left). FIG. 2c (right) depicts an expanded perspective view of a porous flow chamber and a static chamber corresponding to that depicted in cross section in FIG. 2c.

FIG. 2d depicts an assembled device of FIG. 2a mounted on a vacuum manifold.

FIG. 2e depicts an assembled device of FIG. 2a mounted on a flow manifold.

FIG. 2f depicts an exploded perspective view of the device, wherein the device has five layers.

FIG. 2g depicts an assembled device of FIG. 2f.

FIG. 2h depicts a top view of a porous membrane comprising electrodes layer of the device of FIG. 2f.

FIG. 2i depicts an expanded bottom view of a portion of a porous membrane comprising electrodes couple to a flow cell culture layer of the device of FIG. 2f, wherein various components of the porous membrane depicted are illustrated as translucent in order to show the relationship between the porous membrane layer and the flow cell culture layer.

FIG. 2j depicts a histogram showing well-to-well flowrate variation in one embodiment of the device. Percentage of total wells and their deviation from the set flowrate value is shown.

FIG. 2k depicts an exploded perspective view of the device, wherein the device has six layers.

FIG. 3a depicts an exploded perspective view of the device having five layers.

FIG. 3b depicts a perspective view of the assembled device of FIG. 3a, wherein the assembled device is coupled to a flow manifold.

FIG. 3c depicts a schematic side view of the assembled device of FIG. 3b, wherein the outlet of the flow manifold is coupled to a damper, the damper is coupled to a peristaltic pump, and the peristaltic pump is coupled to an inlet in the well block top to facilitate re-circulatory flow of liquid through the assembly (arrows indicate direction of flow).

FIG. 4a depicts an exploded view of one embodiment of the microfluidic device, wherein the device has four layers and is configured for 2D culture.

FIG. 4b depicts a perspective view of an assembled device of the device of FIG. 4a.

FIG. 4c depicts a top view of an assembled device of the device of FIG. 4a.

FIG. 4d depicts a photograph of an assembled device according to the device of FIG. 4a.

FIG. 4e depicts an exploded view of one embodiment of the microfluidic device, wherein the device has five layers and is configured for 3D culture.

FIG. 4f depicts a perspective view of a chamber of a cell culture layer of 4e, wherein cells are provided in the microchannel and the area shown in the light circle corresponds to the portion of the cell culture layer that would be visible if the device were imaged from below.

FIG. 5a depicts an exploded perspective view of a deep well block top and a well block bottom.

FIG. 5b depicts an exploded perspective view of a shallow well block top and a well block bottom.

FIG. 5c depicts an exploded perspective view of a pool well block and a well bottom.

FIGS. 6a-d depict perspective views of embodiments of the cell culture layer of a microfluidic device provided herein.

FIG. 6a depicts a perspective view of a flow cell culture layer.

FIG. 6b depicts a perspective view of a porous flow cell culture layer, comprising a porous membrane (yellow) that is coupled to the bottom surface of a layer of material in which microchannels were cut.

FIG. 6c depicts a perspective view of a static chamber cell culture layer.

FIG. 6d depicts a perspective view of a porous flow cell culture layer, comprising a porous membrane comprising electrodes that is coupled to the bottom surface of a layer of material in which microchannels were cut.

FIG. 7a depicts a imaging base block, which provides direct optical access to each well in the device.

FIG. 7b depicts a perspective view of a flow base block comprising magnetic discs.

FIG. 7c depicts a perspective view of a flow base block lacking magnetic discs.

FIG. 7d depicts an exploded perspective view of one embodiment of the device, wherein the device has five layers, including the flow base block of FIG. 7c.

DETAILED DESCRIPTION OF THE NON-LIMITING EXEMPLARY EMBODIMENTS

Figure 1A:
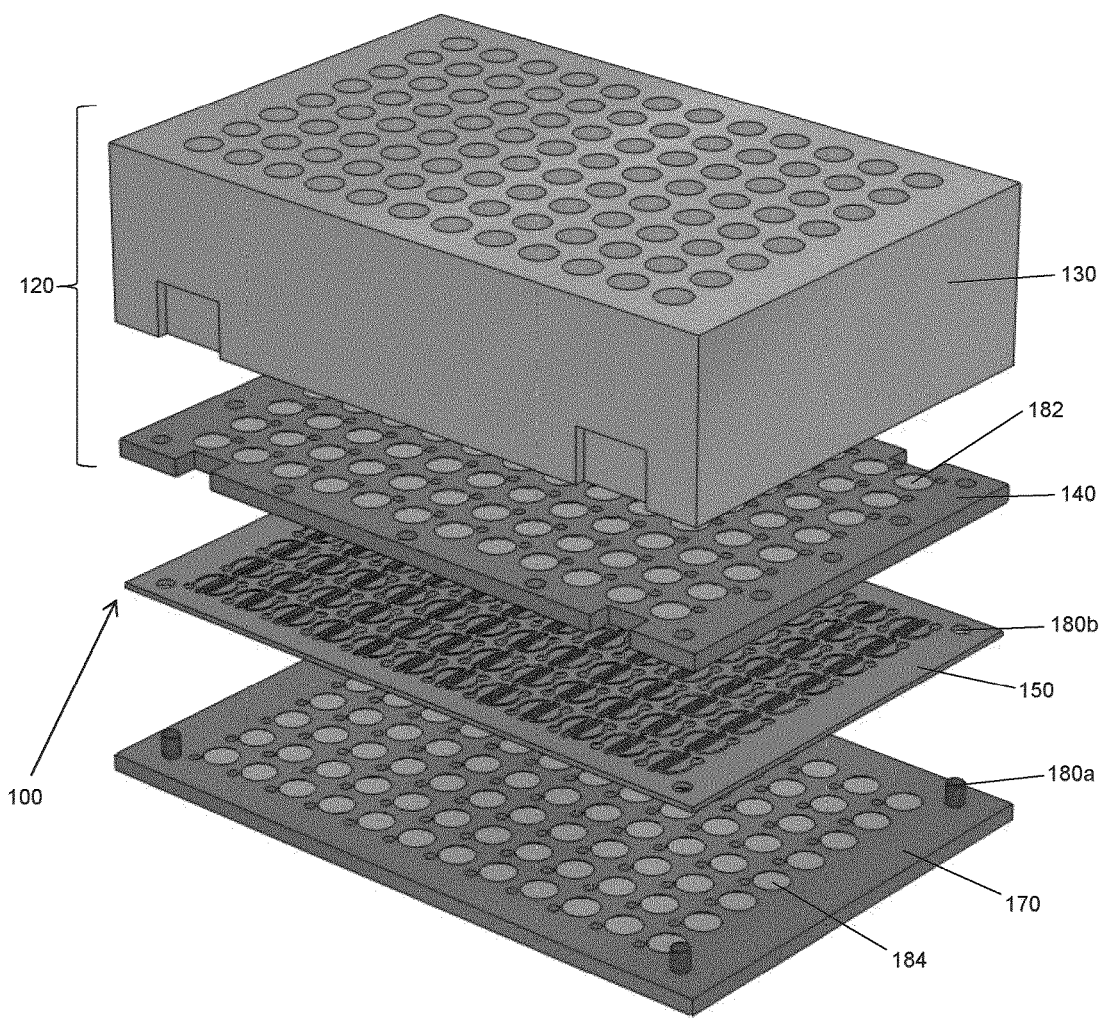
FIGS. 1a-d depict one embodiment of a microfluidic device provided herein, wherein the device is configured for use in a two-dimensional (i.e., 2D) flow assay or cell culture system.

Unless defined otherwise, all technical and scientific terms used herein generally have the same meaning as commonly understood by one of ordinary skill in the art to which this invention belongs.

The present description generally relates to a microfluidic device for cell-based assays and/or cell culture and method for using same. Design of the device is based on that of a standard well plate. Accordingly, the device is suitable for use with equipment designed to handle standard well plates. Each well in the device leads to a discrete culture and/or assay environment. Thus, in one embodiment, the microfluidic device provided herein in a 96-well plate format provides the user with 96 culture microenvironments in which 96 assays may be carried out.

In one embodiment, the device comprises multiple modules that can be arranged to meet specific experimental conditions. In modular embodiments of the device, a user can assemble the device by coupling modules to one another. In one modular embodiment, a kit for assembly of a microfluidic device for cell-based assays and/or cell culture is provided herein.

Modules of the microfluidic device provided herein are classified into five categories: (1) well blocks, which function as a reservoir and/or input site for media, reagents, suspended cells, etc.; (2) cell culture layers, which function as a site for cell culturing and/or cell attachment and provide a means for liquid provided in the well block to contact the cells, under either static or flow conditions; (3) base blocks, which provide a bottom surface for the device; (4) flow control layers, which function to alter the forces provided by liquid as it moves between the well block, cell culture layers and/or base block; and (5) fluid collection layers, which function to collect effluent media from the cell culture layer(s). Upon assembly, the modules are aligned and coupled to form a device. In preferred embodiments, a liquid tight seal is formed between the modules upon assembly, thereby preventing leakage. In various embodiments, a user may assemble and/or disassemble at least part of the device in order to seed cells in the microchannels and/or static chambers and subsequently culture and/or assay the cells.

In one aspect, the microfluidic device is configured for use in dynamic flow-based cell assays and/or culture systems. In one aspect, the microfluidic device is configured for use in static (i.e., no flow) cell assays and/or culture systems. In one aspect, the device can be reconfigured for use in either flow or static cell culture conditions in assay and/or culture systems wherein flow and static conditions may be required in sequence.

In one embodiment, the microfluidic device is configured for use with standard optical imaging devices, such as plate readers.

In one embodiment, the microfluidic device is configured to mimic two dimensional (i.e., 2D) cell culture conditions. In one embodiment, the microfluidic device is configured to mimic three dimensional (i.e., 3D) cell culture conditions.

Aspects and embodiments of the microfluidic device for cell-based assays and/or cell culture provided herein are further described with respect to the drawings.

Two Dimensional Flow Configuration

FIG. 1 depicts one embodiment of the microfluidic device provided herein, wherein the device (100) is configured for 2D flow-based cell assays and/or cell culture. The device (100) provided in the 2D flow configuration can be used to perform assays that mimic in vivo physiological fluid flow conditions, such as, for example, blood flow.

Referring to FIG. 1a, modules included in the 2D flow configuration are (from top to bottom): well block (120), flow cell culture layer (150), and flow base block (170), with a flow control layer comprising a seal (not shown), for example a gasket, provided between each layer (120, 150 and 170) to provide a liquid tight seal between layers of the device (100). In the embodiment shown, the well block (120) comprises a deep well block (130) and a well block bottom (140).

Each module of the device (100) is aligned and coupled to one another. In one preferred embodiment, alignment of the modules is achieved using corresponding mating parts (180a, 180b). In one preferred embodiment, coupling of the modules is achieved using magnetic forces provided by well block magnetic discs (182), base block magnetic discs (184) and the composition of the materials in the well block (120) and the flow base block (170). The magnetic force between the well block (120) and the flow base block (170) clamps the device (100) together.

Figure 1B:
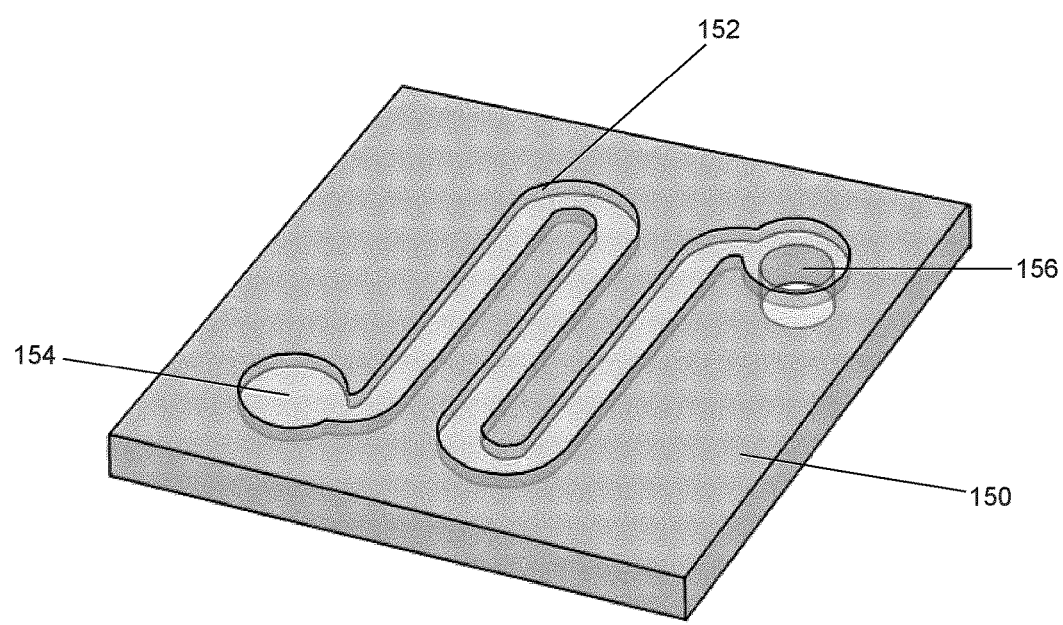

Referring to FIG. 1b, in one embodiment, microchannels (152) in the flow cell culture layer (150) have an elongated serpentine shape that is flanked by an inlet (154) (configured to communicate with an adjacent module, e.g., a well block (120)) and an outlet (156) (configured to communicate with an adjacent module, e.g., a flow base block (170)).

Figure 1C:
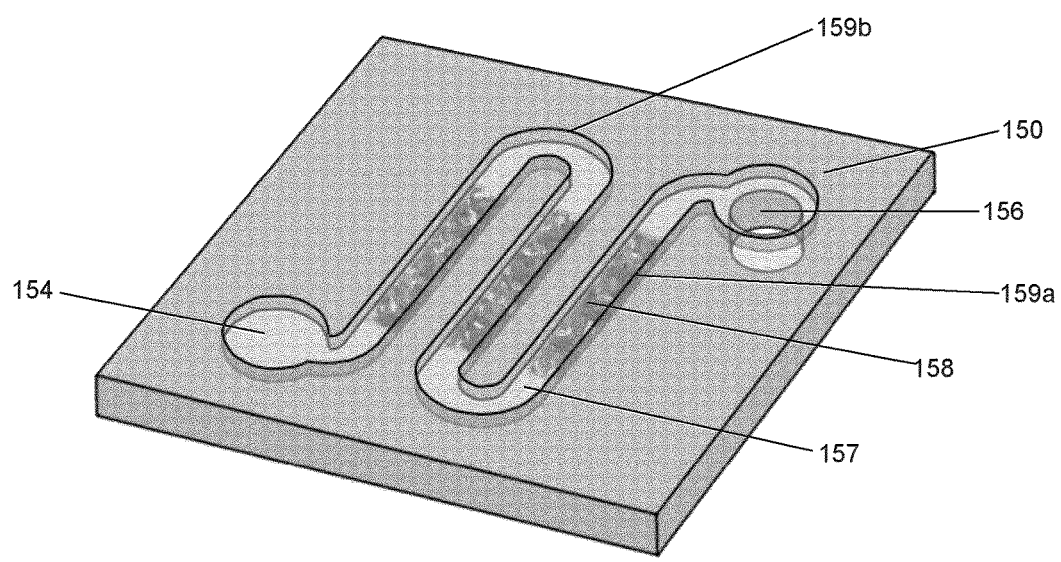

Referring to FIG. 1c, in one embodiment, a user provides cells (158) onto the flow cell culture layer (150) so that the cells (158) may adhere to an internal bottom surface (157) in the microchannels (152) of the flow cell culture layer (150). Cells may be provided to the microchannels (152) in the flow cell culture layer (150), for example, using standard techniques (e.g. pipetting). In preferred embodiments, cells (158) are provided only to elongated sections (159a) of the serpentine-shaped microchannel (152), rather than curved sections (159b) of the serpentine-shaped microchannel (152) such that in operation they will be exposed to constant shear stress provided by fluid flowing through the microchannels (152).

Figure 1D:
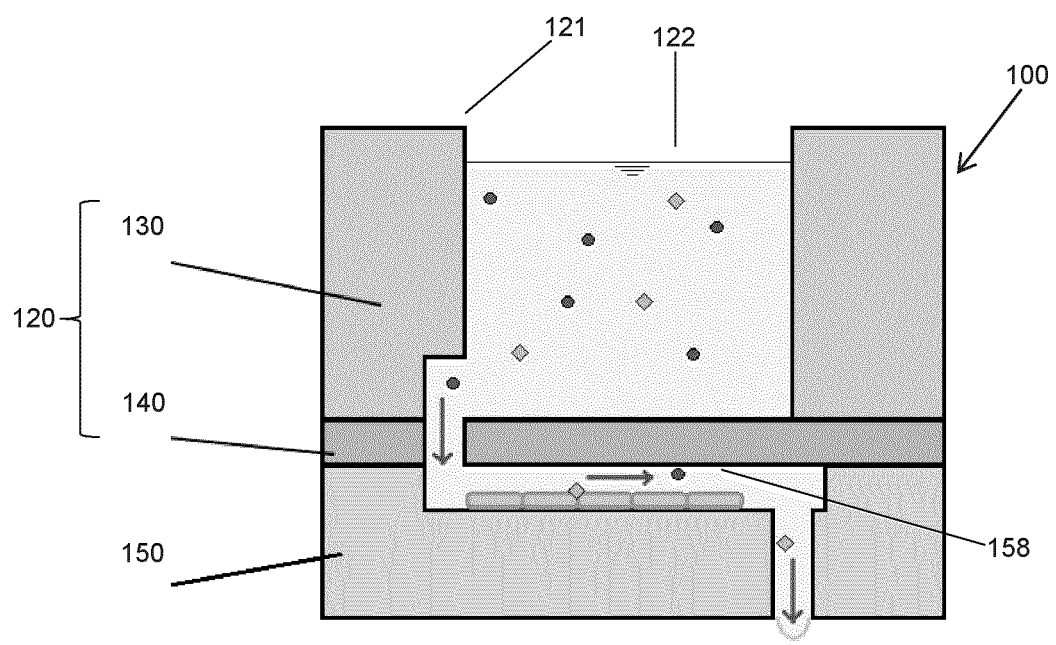

Referring to FIG. 1d, once cells (158) are seeded on the flow cell culture layer (150), the device (100) may be assembled and a liquid (122) may be provided into each well (121) of the well block (120), for example, using standard techniques (e.g. pipetting). The assembled device (100), seeded with cells (158) and liquid (122), may be coupled to either a vacuum manifold (not shown), which provides air pressure-induced flow, or a fluid manifold (not shown), which provides fluid pump-induced flow of liquid from each of the plurality of wells (121) in the well block (120) through the microchannels (152) of the flow cell culture layer (150) and into the flow base block (170), allowing cells (158) seeded in the microchannels (152) to be exposed to active fluid flow at a rate that can be controlled by the user (direction of fluid flow is illustrated by arrows in FIG. 1d).

Three Dimensional Flow Configuration

FIG. 2 depicts one embodiment of a microfluidic device provided herein, wherein the device (200a, f, k) is configured for use in a three dimensional (i.e., 3D) flow assay or cell culture system. The 3D configuration of the device (200a, f, k) (also referred to herein as a "co-culture" configuration) provides increased physiological fidelity relative to the 2D configuration for the device (100), at least because the 3D configuration of the device (200a, f, k) enables interactions between different cell types. The device (200a, f, k) provided in the 3D flow configuration can be used to perform assays that mimic in vivo physiological fluid flow conditions found in tissues, such as, for example, vascularized tissues.

Figure 2A:
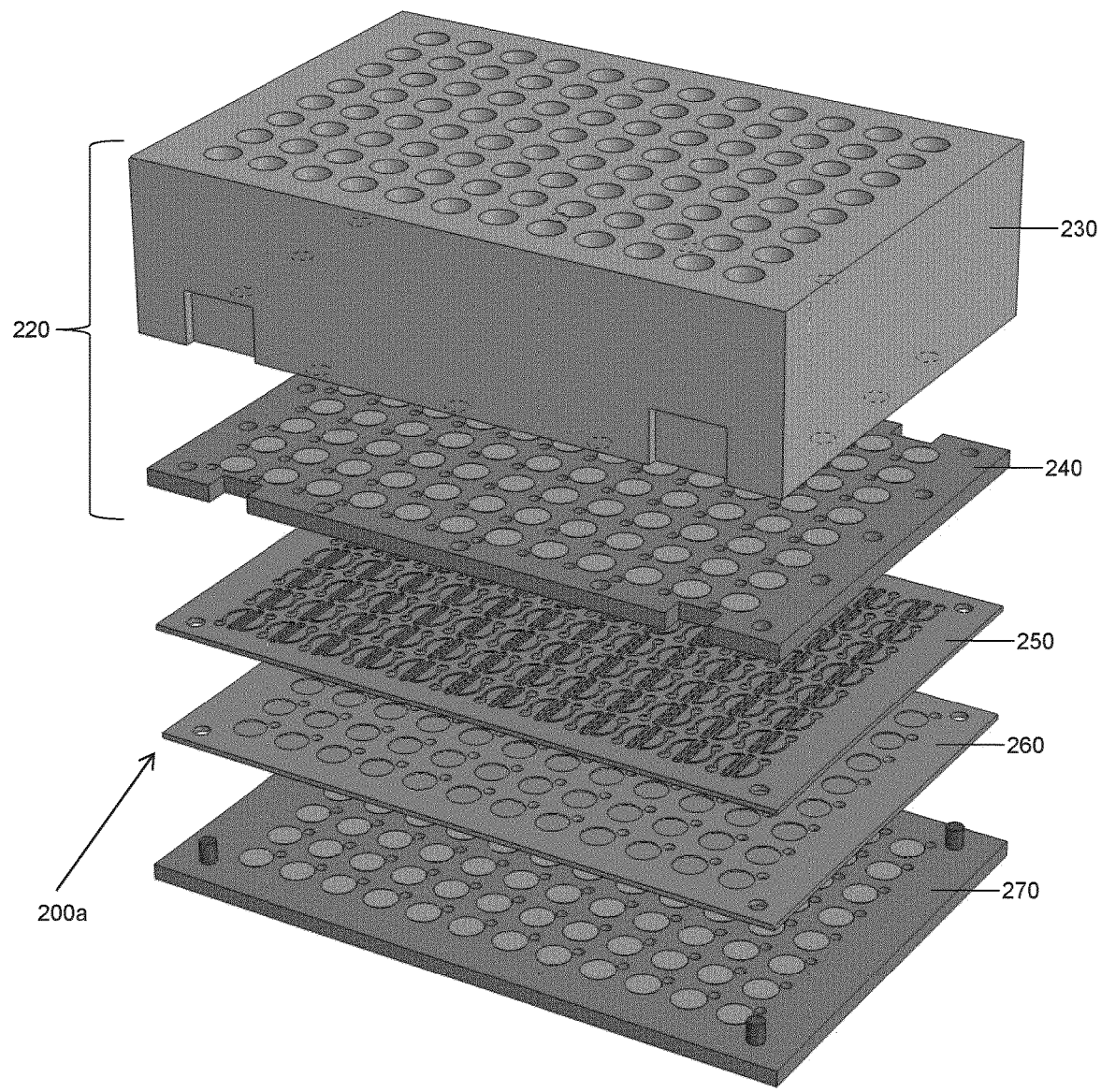

Referring to FIG. 2a, which depicts an exploded perspective view of the device (200a), in one embodiment, the device has five layers: (from top to bottom) a well block top (230), a well block bottom (240), a first cell culture layer (250) (i.e., a porous flow chamber), a second cell culture layer (260) (i.e., static chamber) and a base block (270). In operation, seals would be provided between the well block (220) and first cell culture layer (250) and the second cell culture layer (260) and the base block (270) to maintain a liquid tight seal. A thin layer (not shown; e.g., a PDMS thin layer) may be provided between the first and second cell culture layers (250, 260) to, at least in part, provide a seal there between.

Figure 2B:
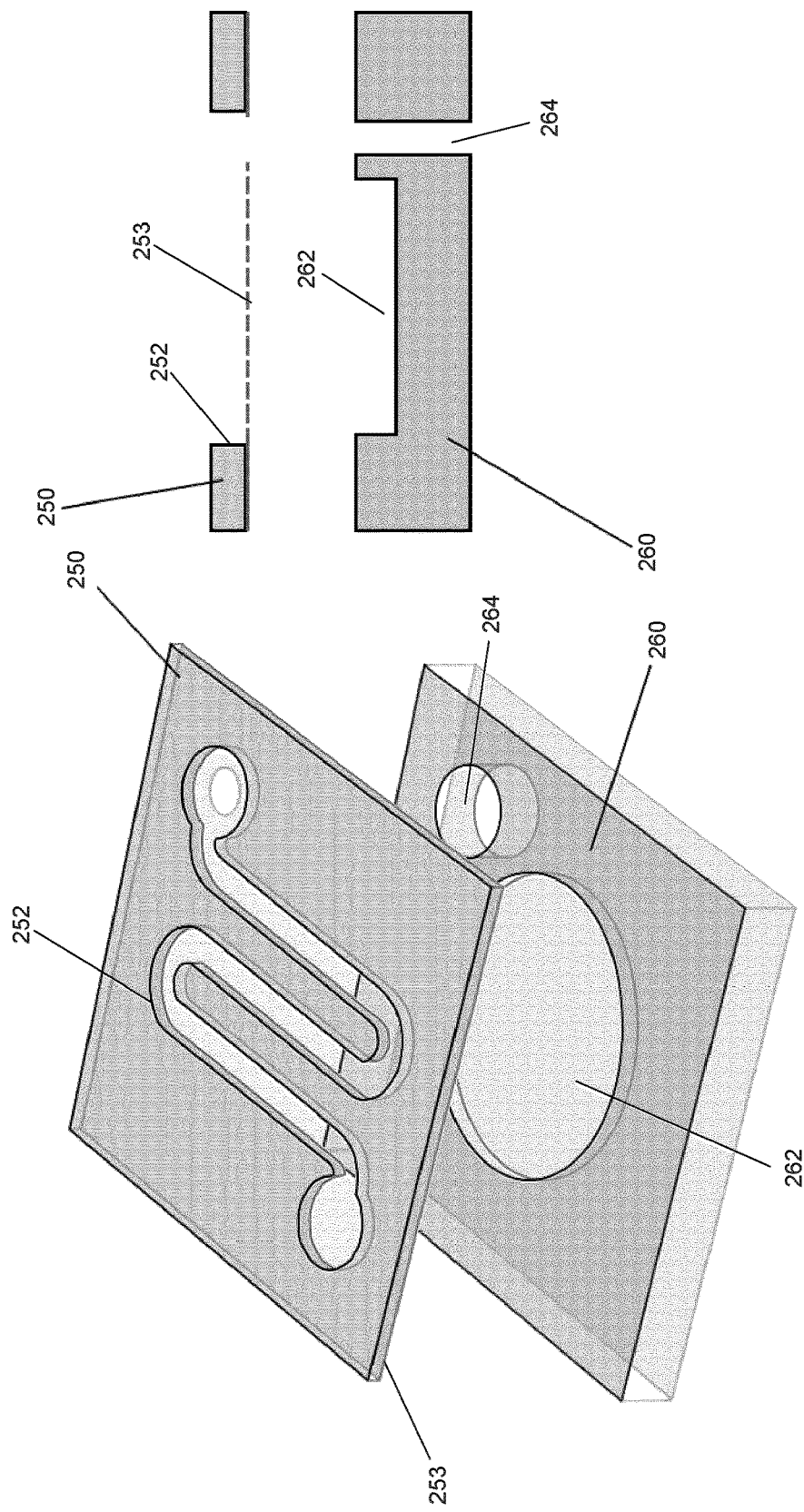

FIG. 2b depicts an expanded exploded perspective view of one of a plurality of microchannels (252) and corresponding porous membranes (253) in the first cell culture layer (i.e., porous flow chamber; upper left), an exploded perspective view of one of a plurality of static cell culture chamber wells (262) and corresponding outlets (264) in the second cell culture layer (260) (i.e., static chamber; lower left), a cross-sectional side view of a microchannel (252) and porous membrane (253) (right upper), and a static cell culture chamber well (262) and corresponding outlet (264) (right lower). As in the 2D flow configuration, a user may seed a first cell type onto a bottom surface of the microchannels (252) in the first cell culture layer (250) (i.e., porous flow chamber), the bottom surface being provided by a porous membrane (253). The user may provide a second cell type (not shown) into a static cell culture chamber well (262) in the second cell culture layer (260). The second cell type may be the same or different from the first cell type and it may be provided in various media, such as, for example, cell culture media, buffer or a hydrogel composition.

Figure 2C:
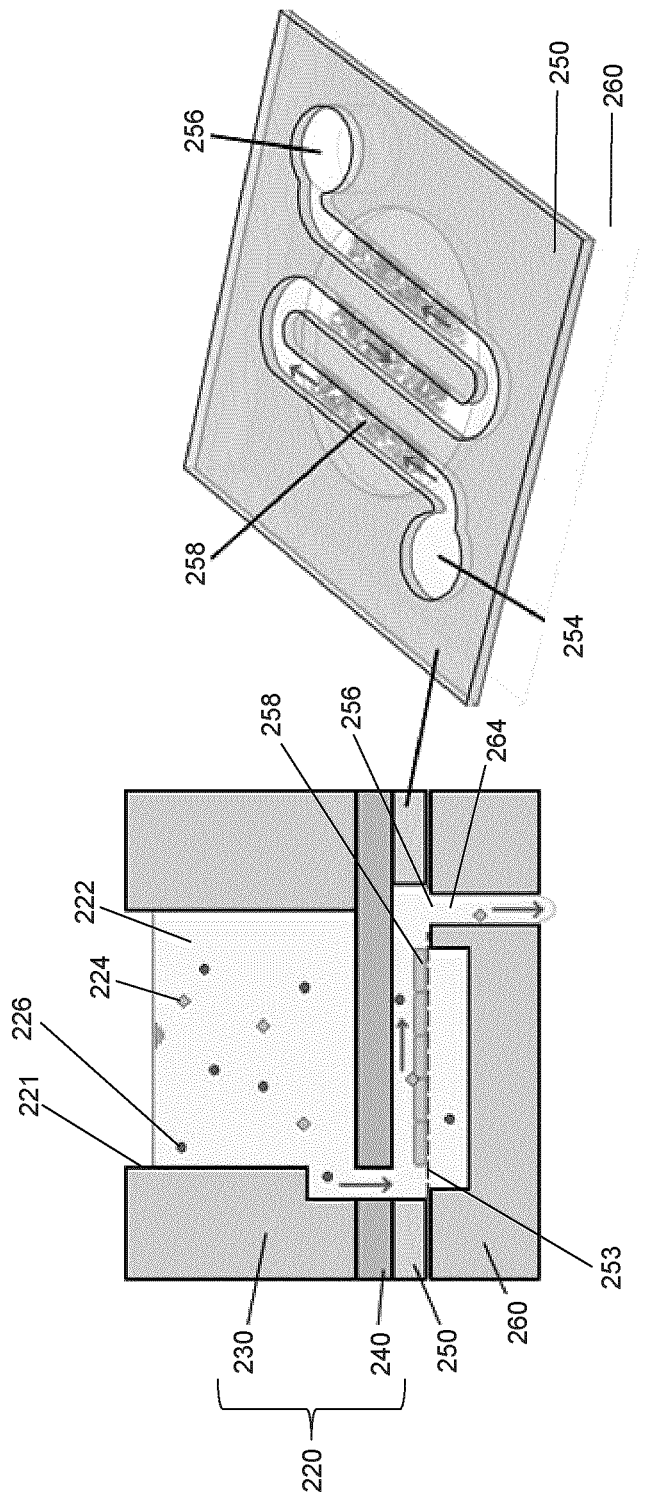

FIG. 2c (left) depicts a cross-sectional side view of one well (221) of the assembled device (200a) of FIG. 2, wherein the well (221) comprises media (222) (blue liquid), reagents (224) (green diamonds) and suspended cells (226) (red circles) and a first cell type (258) provided in a layer (pink) on the porous membrane (253) portion of the first cell culture layer (250) (i.e., porous flow chamber). The arrows indicate directional flow of liquid from the well block (220) through the first cell culture layer (250), over the monolayer of cells (258) and the outlet of the first and second cell culture layers (256 and 264, respectively) (left). FIG. 2c (right) depicts an expanded perspective view of the first cell culture layer (250) and the second cell culture layer (260) corresponding to that depicted in cross section in FIG. 2c.

In operation, the device (200a) is assembled and a liquid (222) is provided into each well (221) of the well block (220). The assembled device (200), seeded with the first cell type (258) and fluid (222), is coupled to either a vacuum manifold (290), which provides air pressure-induced flow, or a fluid manifold (296), which provides fluid pump-induced flow of liquid from each of a plurality of wells (221) in the well block (220) through the microchannels (252) of the first cell culture layer (250) and into the base block (270), allowing the first cell type (258) seeded in the microchannels (252) to be exposed to active fluid flow at a rate that can be controlled by the user and protecting the second cell type (not shown) provided in the static cell culture chamber well (262) of the second cell culture layer (260) from flow. The porous membrane (253) and optional thin PDMS layer between the first cell culture layer (250) and the second cell culture layer (260) facilitate movement of cell secretions and/or cells between the layers (250, 260), similar to the movement that may be found in a 3D vascular environment. The 3D flow configuration of the device (200) enables study of cell transmigration, drug permeability, and interaction between endothelial/epithelial cells with underlying tissue. The 3D flow configuration of the device (200) has a wide range of potential applications in drug and toxicology screening using various cell types (e.g., hepatocytes, vascular smooth muscle cells, cardiomyocytes, tumor stromal cells, brain cells, gut cells, etc.).

Figure 2D:
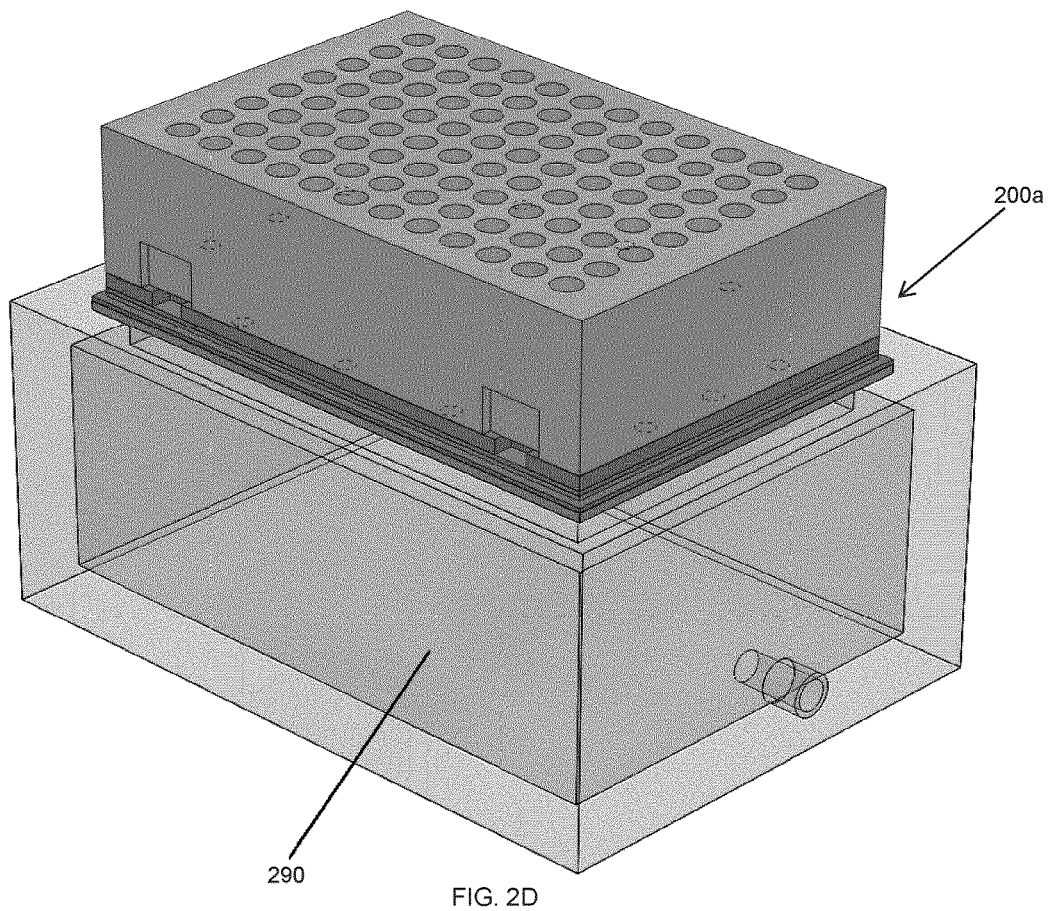
Figure 2E:
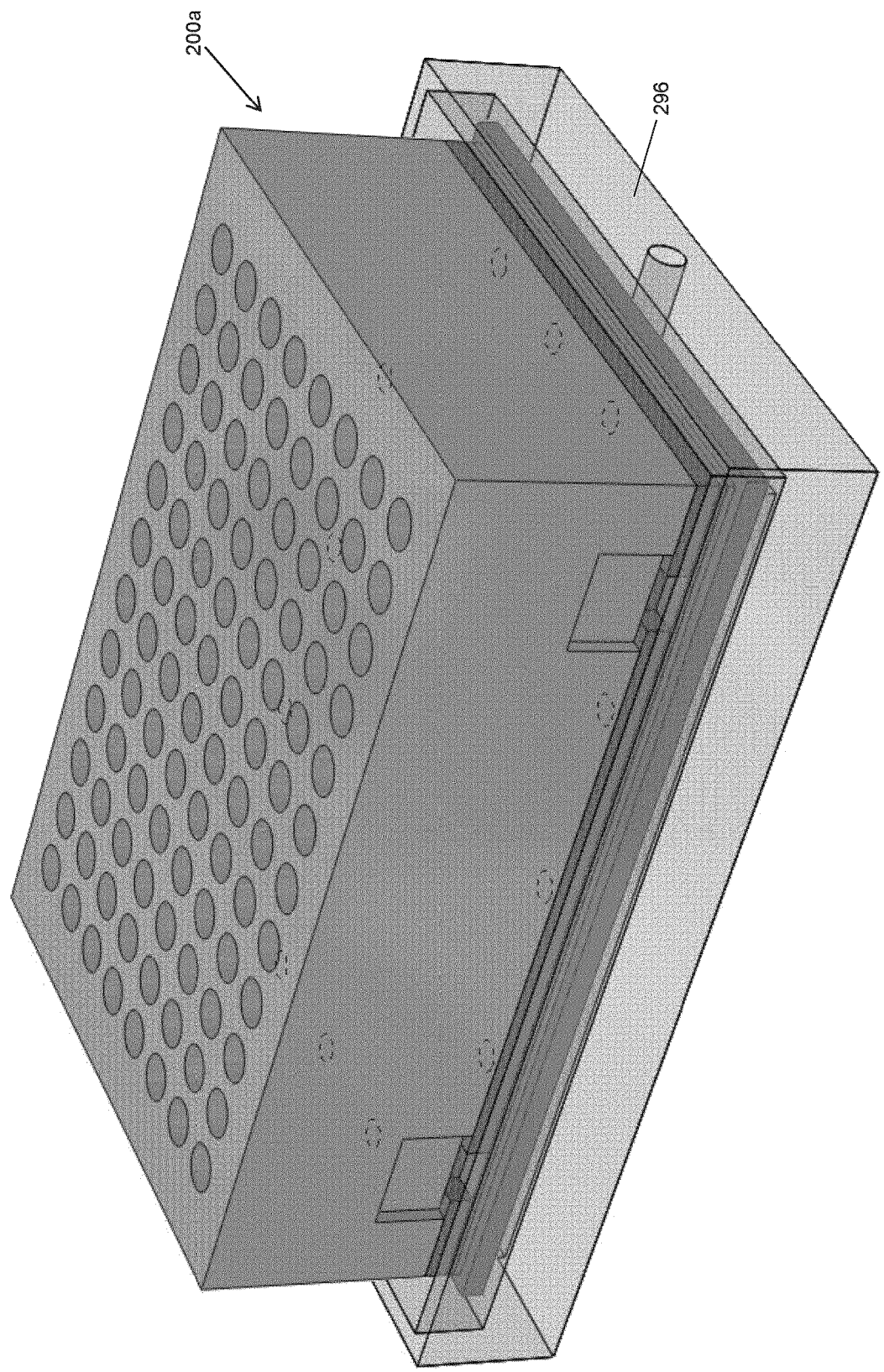

In one embodiment, the assembled device (200a) is coupled to a vacuum manifold (290), which is connected to a pressure regulator (not shown) that controls the negative air pressure in the vacuum manifold (290) (FIG. 2d). The pressure difference between the well block (220) (atmospheric) and the device's outlets (not shown; located on the base block (270) drives the fluid from each of the plurality of wells (221) and through the microfluidic channels (252) of the cell culture layer (250). The fluid then exits the microfluidic channels via the microchannel outlet (256) and the static cell culture chamber well outlet (264) and moves through the base block (270) and into the vacuum manifold (290) where it pools for the duration of the experiment. Typically, the vacuum pressure required to induce flow at a physiological rates is low (i.e. in a range of about −0.5 to −1 kPa). To improve flow rate control and stability, a filter can be added between the first cell culture layer (250) and the base block (270) to increase flow resistance allowing for lower vacuum pressures (i.e., in a range of about −20 to −50 kPa) negating any flow fluctuations caused by the pressure head from the liquid in the well block (220). One advantage of this configuration is that the combined effluent from the microchannels (252) can be collected from the vacuum manifold (290) for further analysis and, with appropriate filter substrate, selection proteins absorbed to the filter can be analyzed on an individual well basis.

In one embodiment, the assembled device (200a) is coupled to a fluid manifold (296), (FIG. 2e), which is connected to a pump (not shown) through a flow damper (not shown). Much like the air pressure assembly described above, fluid is driven from the well block (220), through the microchannels (252) of the first cell culture layer (250), into the base block (270) and then into the fluid manifold (296). Unlike the air pressure assembly, the flow manifold (296) is completely filled with fluid, and the connected pump (not shown) has the capacity to drain the fluid at a constant rate. This assembly allows the user to directly set flow rates in the microchannels (252) by adjusting the pump rate (a relationship curve between pressure and flow-rate is not needed) and allows for a substantially equal flow rate across all wells (221) and the corresponding microchannels and/or chambers of the cell culture layers (250 and 260). Further, because liquid cannot be compressed, microchannel flow rates can be accurately controlled by a pump, thereby allowing for complex physiological flow waveforms.

Figure 2F:
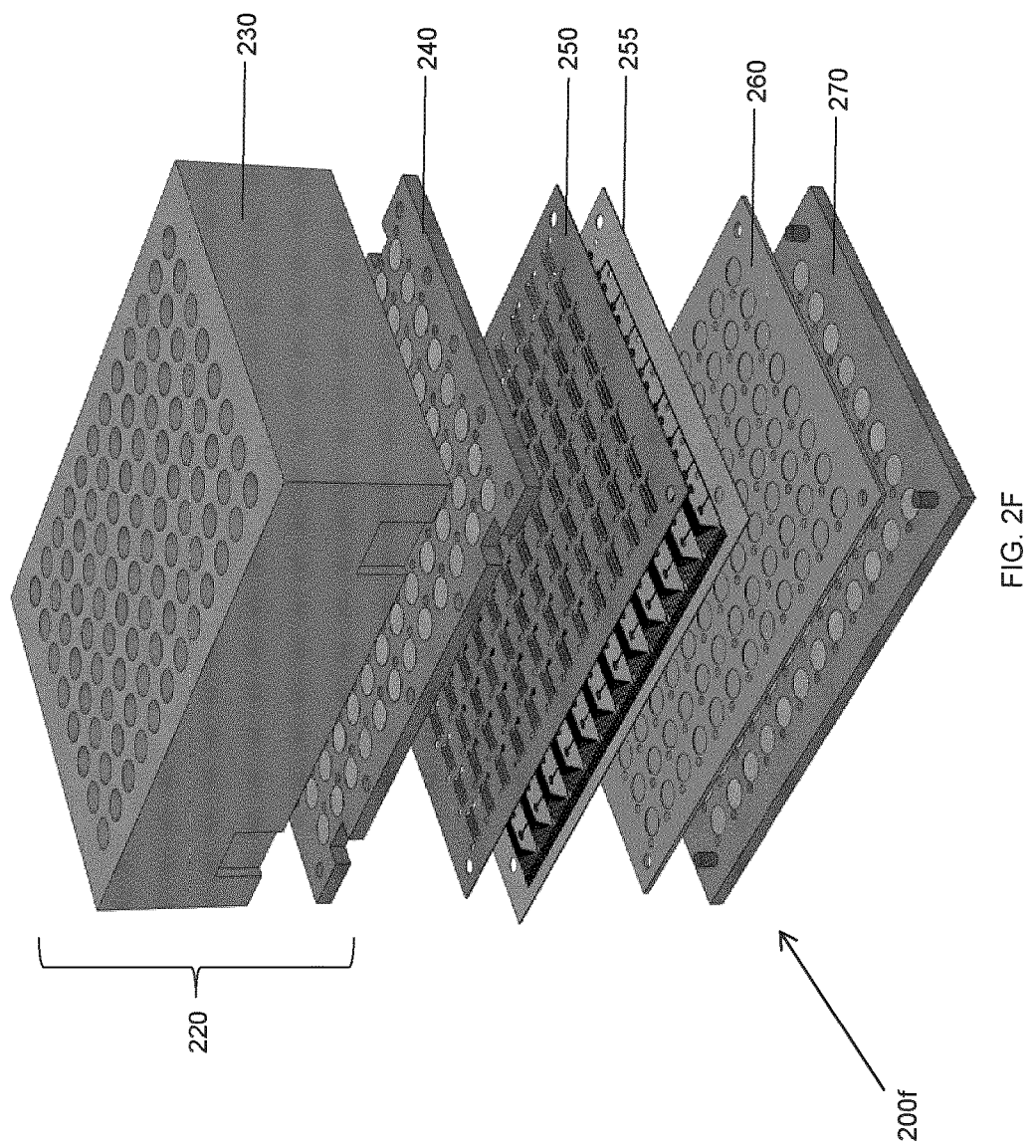
Figure 2G:
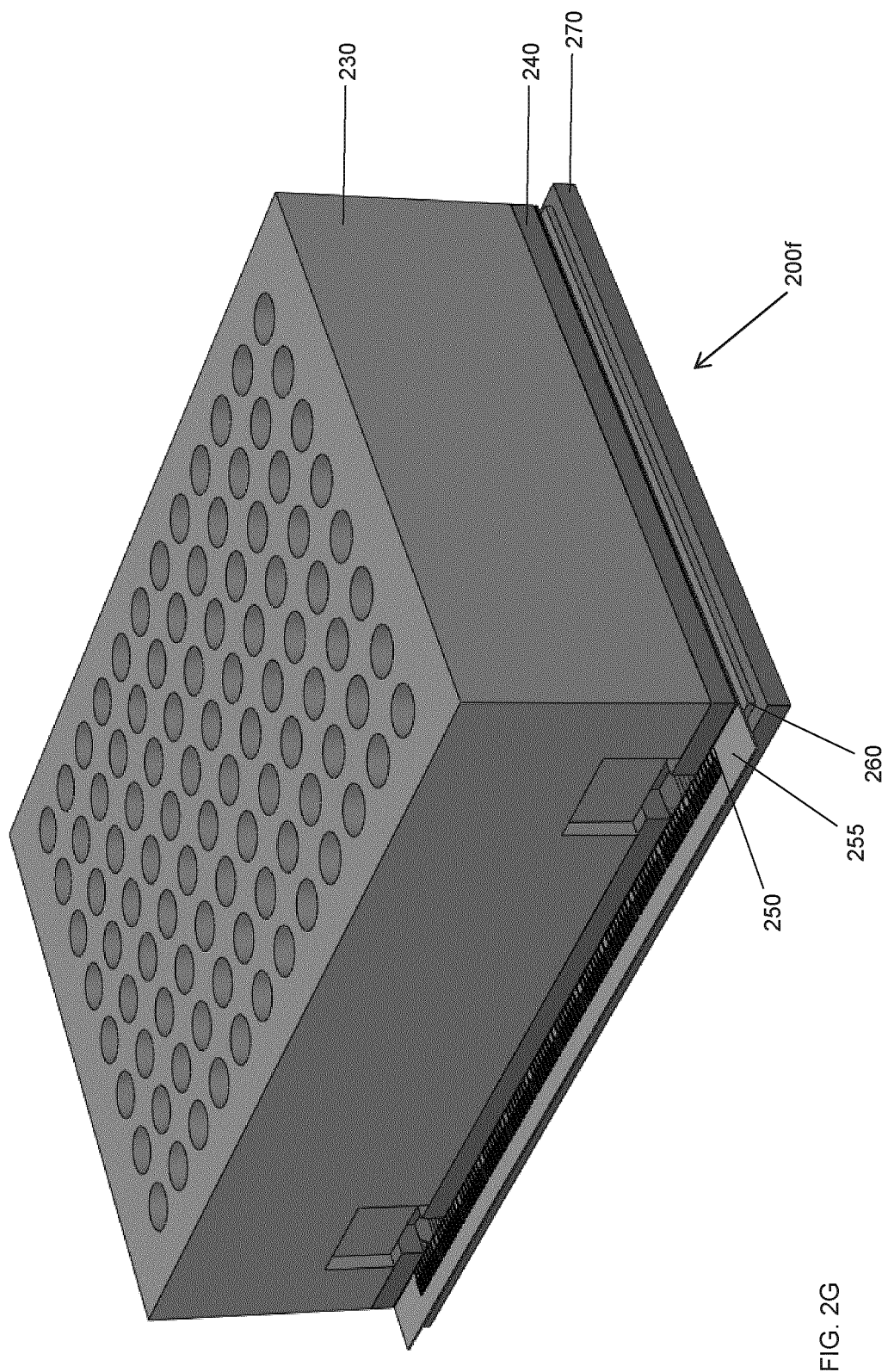

Referring to FIG. 2f, which depicts an exploded perspective view of the device (200f), in one embodiment, the device (200f) has five layers: (from top to bottom) a well block top (230), a well block bottom (240), a first cell culture layer (250) (i.e., a porous flow chamber), which is coupled to a porous membrane comprising electrodes (255), a second cell culture layer (260) (i.e., static chamber) and a base block (270). In operation, seals would be provided between the well block (220) and first cell culture layer (250) and the second cell culture layer (260) and the base block (270) to maintain a liquid tight seal. The porous membrane comprising electrodes (255) would be sealably coupled to the bottom surface of the first cell culture layer (250). A thin layer (not shown; e.g., a PDMS thin layer) may be provided between the porous membrane comprising electrodes (255) and the second cell culture layer (260) to, at least in part, provide a seal there between. A perspective view of the assembled device of FIG. 2f is provided in FIG. 2g.

Figure 2H:
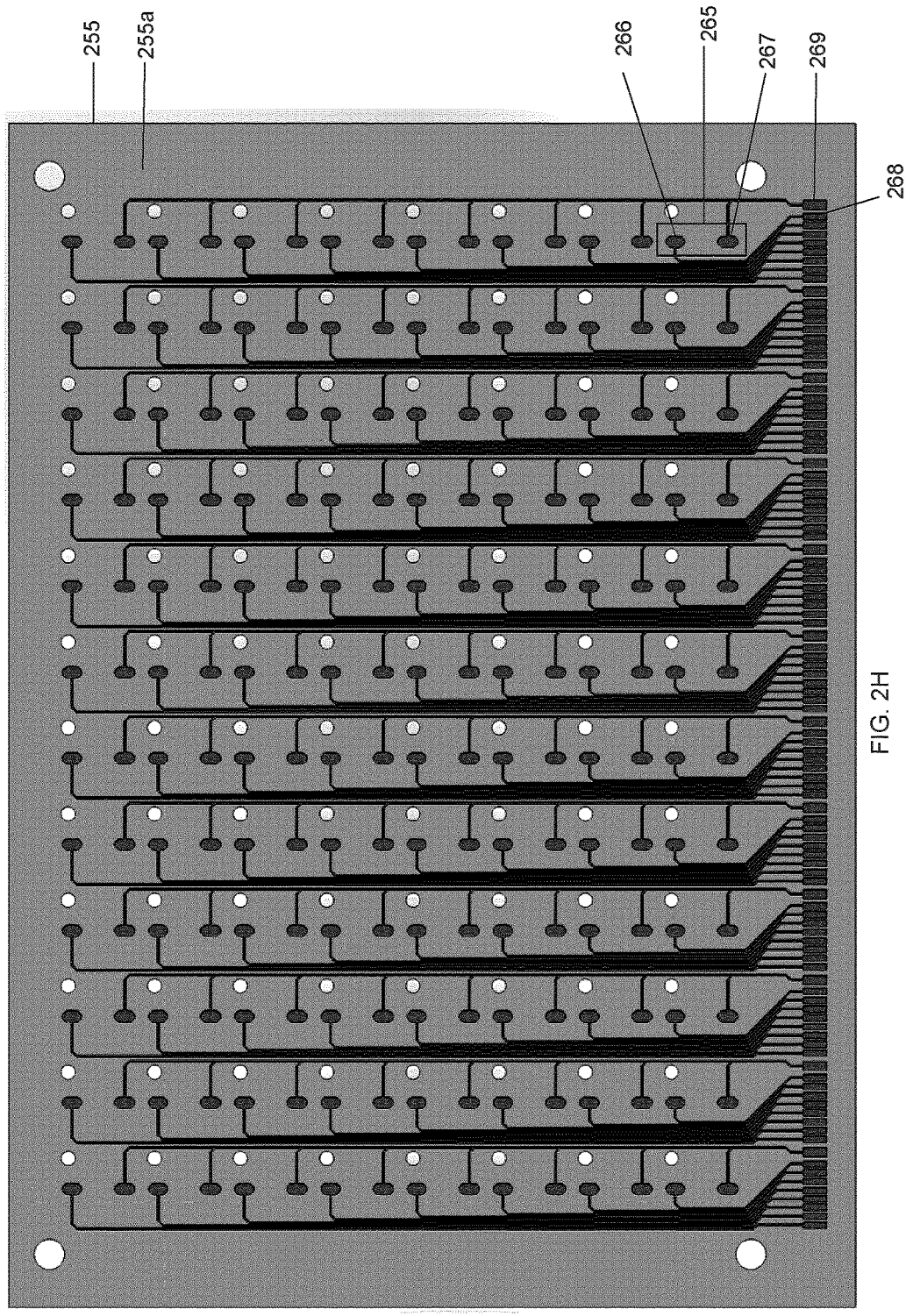

Referring to FIG. 2h, which depicts a top view of a porous membrane comprising electrodes (255), in one embodiment, the porous membrane comprising electrodes (255) comprises a plurality of 2 cell electrode pairs (265), each electrode pair (265) disposed on a top surface (255a) of the porous membrane comprising electrodes (255), such that it corresponds to one of the microchannels of the first cell culture layer (250) when the first cell culture layer (250) and porous membrane comprising electrodes (255) are coupled together. Each electrode pair (265) comprises an anode (267) and cathode (266) that are each connected to a respective connector electrode pair. In the illustrated embodiment, there is one connector cathode (268) corresponding to each cell cathode (266) and one connector anode ((269) per 8 cell anodes (267) (i.e., one connector anode per row of microchannels (252). The connector electrodes (268, 269) serve as conductive pads to connect to a cable (e.g., a ribbon cable) that may then be connected to peripheral equipment (e.g., ECIS controller; voltage generator).

Referring to FIG. 2i, which depicts an expanded bottom view of a portion of a porous membrane comprising electrodes (255) coupled to a bottom surface of a first cell culture layer, wherein the porous membrane comprising electrodes (255) illustrated is transparent, such to illustrate the relationship between the coupled porous membrane comprising electrodes (255) and the first cell culture layer. In operation, cells may be grown within the microchannel (252) on a top surface of the porous membrane comprising electrodes (255). A user may apply alternating current to one or more sets of electrodes (266, 267) and determine a range of electrical impedance (for a range of AC frequency), which a user may then correlate with one or more cell characteristic, such as, for example, cell confluency, permeability, density, function, etc.

Figure 2J:
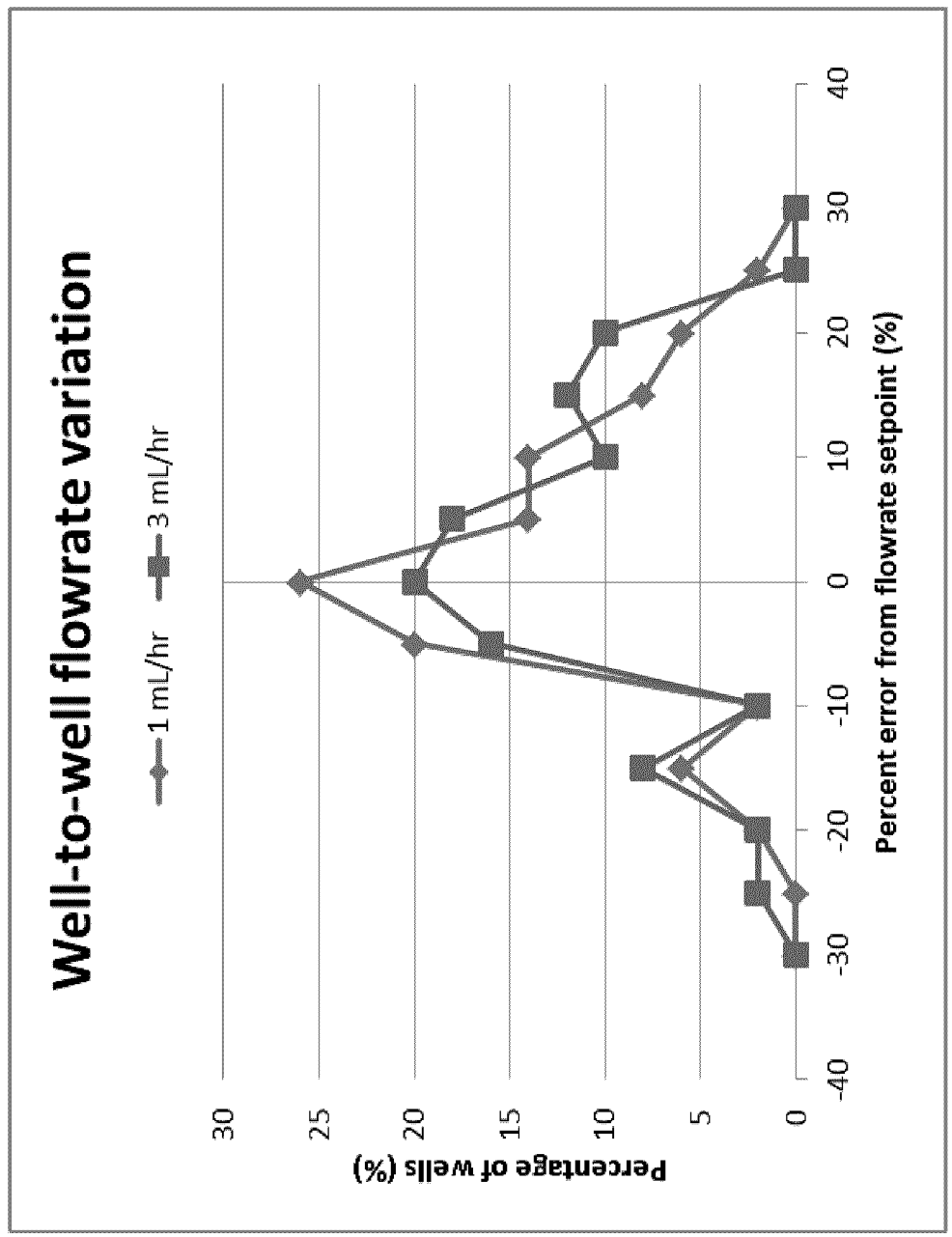

Well-to-well flowrate variation in the embodiment of the device provided in FIGS. 2f-2i is provided in FIG. 2j. The set flowrates (1-3 mL/hr) were within maximum operating range of the device (i.e., shear stresses up to 10 dynes/cm$^2$). Flowrate data were calculated by measuring the remaining volume in each well of the deep well block and averaging over the duration of the experiment.

Figure 2K:
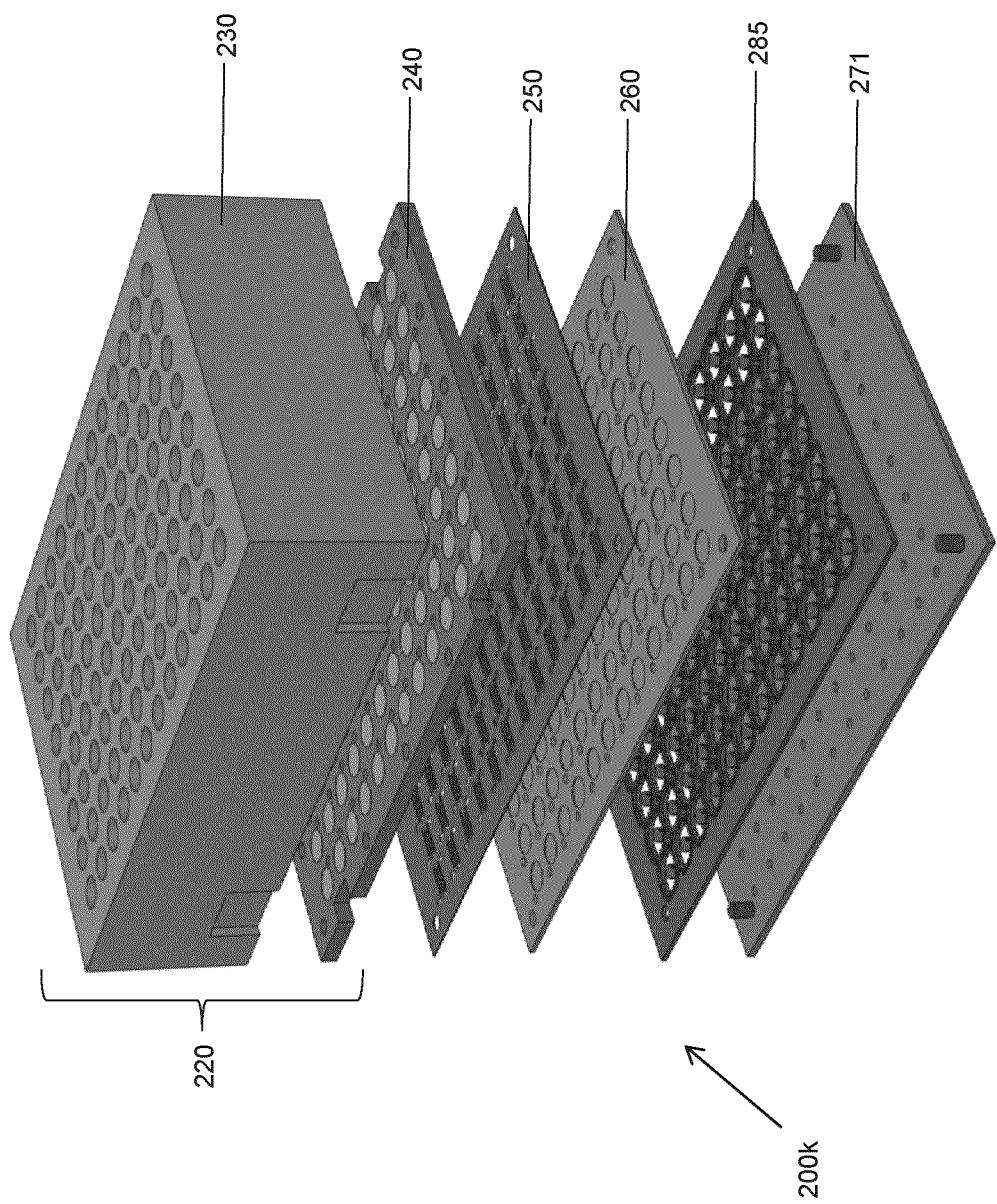

Referring to FIG. 2k, which depicts an exploded perspective view of the device (200k), in one embodiment, the device (200k) has six layers: (from top to bottom) a well block top (230), a well block bottom (240), a first cell culture layer (250) (i.e., a porous flow chamber), a second cell culture layer (260) (i.e., static chamber), a fluid collection layer (285) and a base block (270). In operation, seals would be provided between the well block (220) and first cell culture layer (250) and the fluid collection layer (285) and the base block (270) to maintain a liquid tight seal. The fluid collection layer (285) would be sealably coupled to the bottom surface of the second cell culture layer (260). A thin layer (not shown; e.g., a PDMS thin layer) may be provided between the first cell culture layer (250) and the second cell culture layer (260) to, at least in part, provide a seal there between.

Figure 2L:
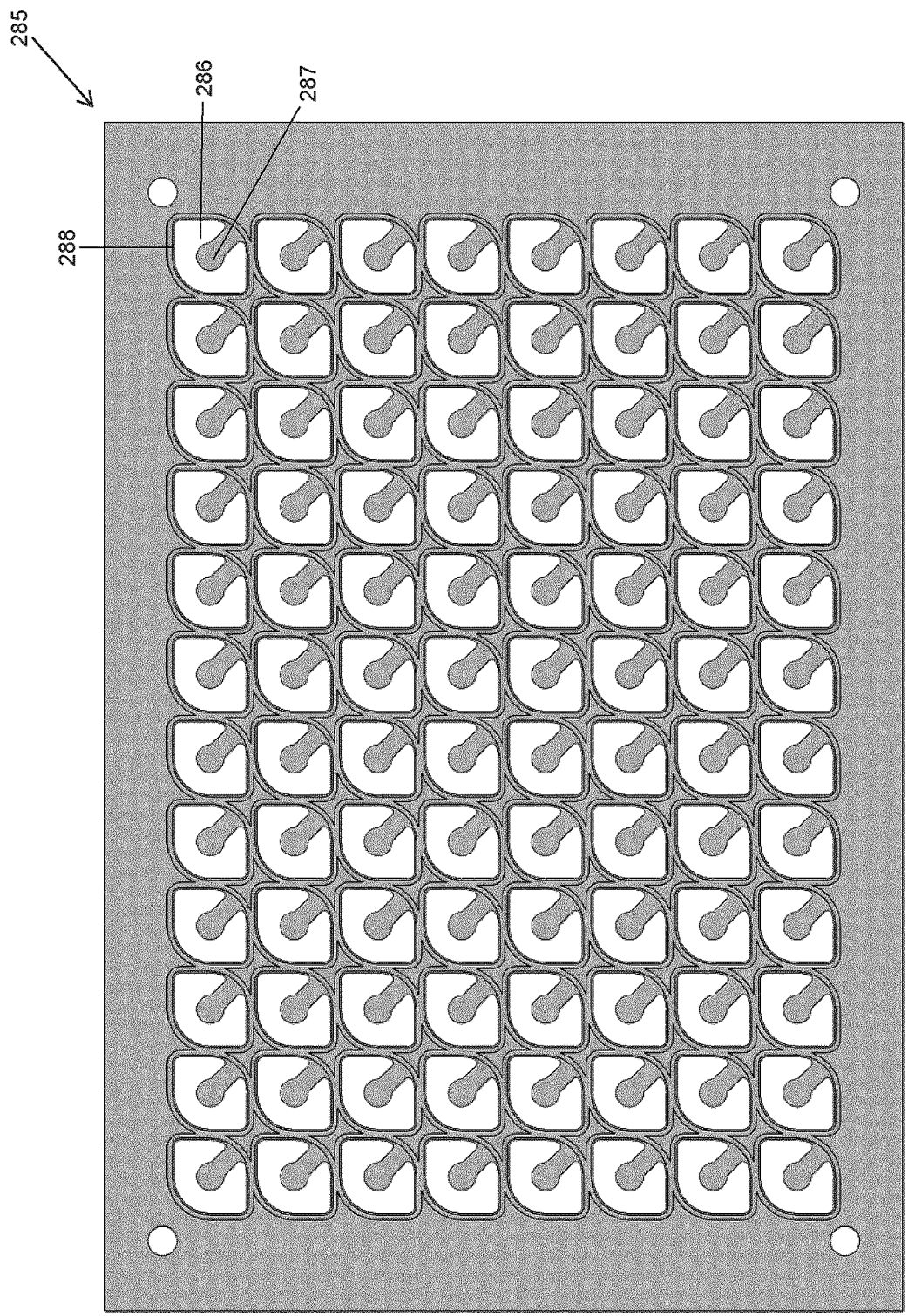
FIG. 2l depicts a top view of a fluid collection layer of the device of FIG. 2k.

Referring to FIG. 2l, which depicts a top view of a fluid collection layer (285), in one embodiment, the fluid collection layer (285) comprises a plurality of bottomless chambers, each bottomless chamber being disposed in the fluid collection layer (285), such that it corresponds to one of the microchannels of the first cell culture layer (250) and/or one of the static cell culture chamber wells (262) of the second cell culture layer (260) when the first cell culture layer (250) and/or the second cell culture layer (260) and the fluid collection layer (285) are coupled together. In the embodiment illustrated in FIG. 2l, each bottomless chamber comprises a projection extending from a wall of the bottomless chamber into the bottomless chamber, the projection extending in the plane of the fluid collection layer. In one embodiment, the projection functions to maintain space in the bottomless chamber when a second cell culture layer is disposed thereupon.

Figure 2M:
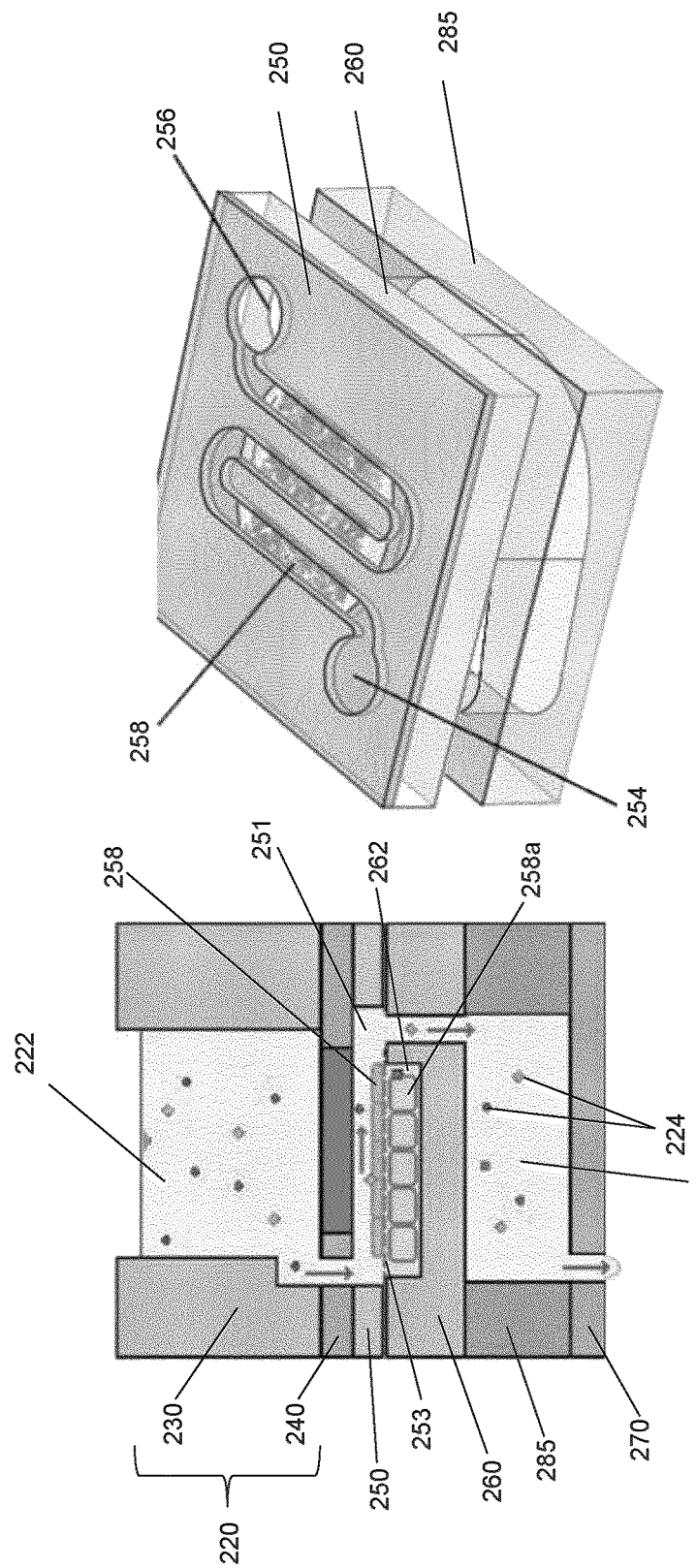
FIG. 2m (left) depicts a cross-section of a single well in the assembled device of FIG. 2k (not to scale). An isometric view of a single well of the assembled device of FIG. 2k (without the well and base block) is also provided (right).

Referring to FIG. 2m (left), which depicts a cross section of a single well in the assembled device of FIG. 2k, and FIG. 2m (right), which depicts an isometric view of a single well in the assembled device of FIG. 2k (without the well and base blocks), endothelial cells (258) are grown in the flow channel on top of a porous membrane (253). The static cell culture chamber well (262) contains a 3D microtissue seeded with tissue specific cells (258a). In operation, cell culture medium, optionally comprising one or more drugs or other reagents, is flown from the well block (230 and 240) through the flow chamber (251) and into the fluid collection chamber (286) and manifold (not shown). Cell secreted components (e.g., proteins or signaling factors (purple squares)) diffuse into the flowing stream of media and are carried to the fluid collection chamber (286). Media in the fluid collection chamber (286) can be then sampled.

In operation, effluent media from a flow culture experiment can be collected in the fluid collection layer of the device. A user can then analyze the effluent media from one or more fluid collection chambers to determine, for example, what components were secreted by cells in the microchannels (252) and/or static cell culture chambers (262).

Recirculatory Flow Configuration

FIG. 3 depicts one embodiment of a microfluidic device provided herein, wherein the device (300) is configured for use in a recirculatory flow assay or cell culture system. Recirculatory configurations are designed to allow a user to condition cells to flow for an extended period of time, thereby allowing the cells to "acclimatize" to a dynamic flow environment. For example, a prolonged pre-conditioning period under active flow conditions can have consequences for a cell's responsiveness to various drug candidates (e.g., endothelial cells). A recirculatory flow configuration may be provided to a 2D or 3D flow configuration of cell culture layers.

Figure 3A:
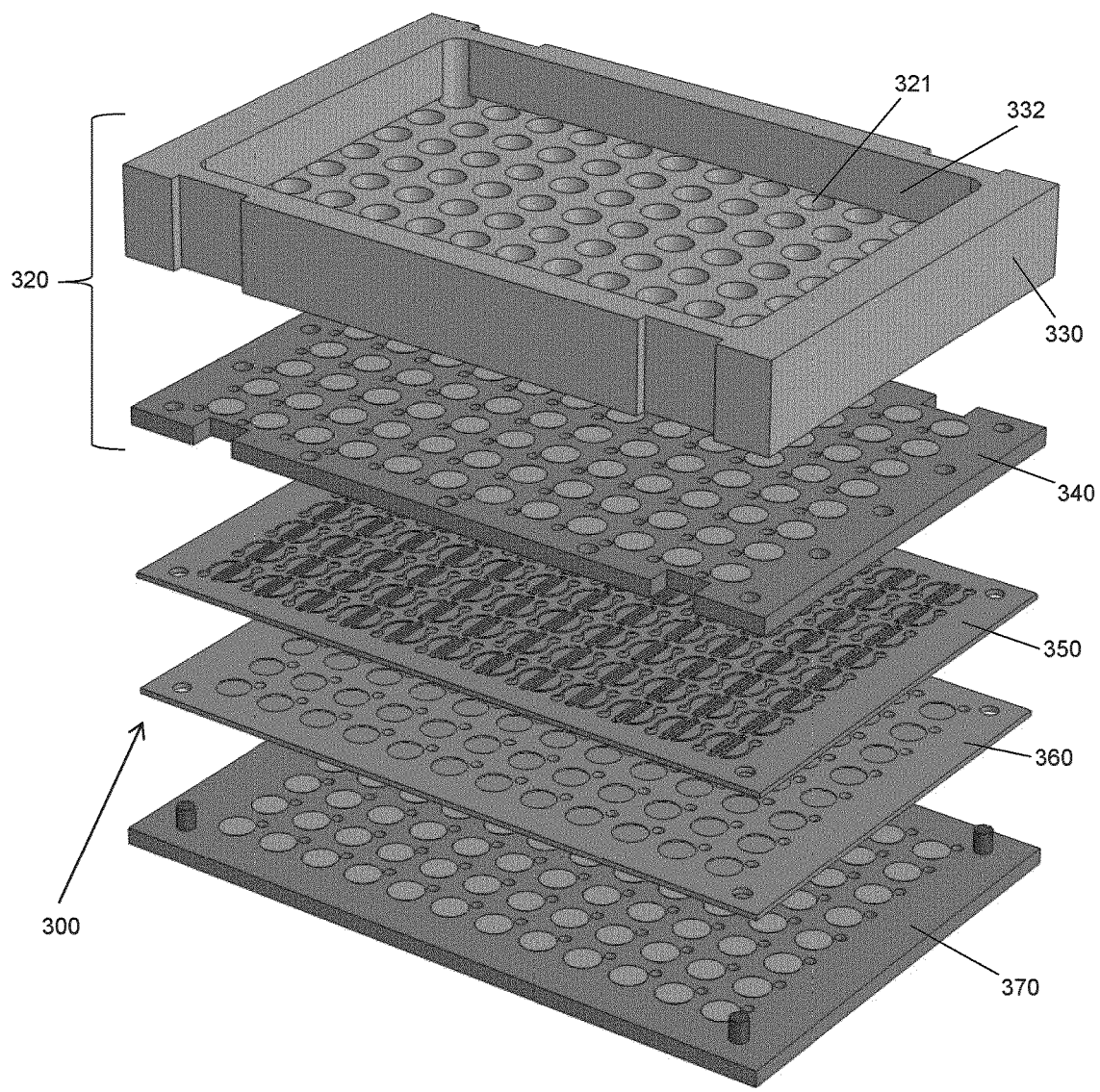
FIGS. 3a-c depict one embodiment of a microfluidic device provided herein, wherein the device is configured for use in a re-circulatory 3D flow cell assay or cell culture system.

Referring to FIG. 3a, which depicts an exploded perspective view of one embodiment of the device (300), five layers are provided in the device (top to bottom): a pool well block top (330), well block bottom (340), a first cell culture layer (350) (i.e., a flow chamber), a second cell culture layer (360) (i.e., a static chamber) and base block (370). In operation, seals (not shown) would be provided between the well block (320) and first cell culture layer (350) and the second cell culture layer (360) and the base block (370) to maintain a liquid tight seal. A thin PDMS layer may be provided between the cell culture layers (350, 360) to provide a seal there between. A well block (320) comprising a pool well block top (330) comprises a bottomless tray (332) that provides a pooling area for liquid that can move through each of a plurality of wells (321) situated below the bottomless tray (332) portion of the pool well block top (330). A pool well block top (330) facilitates long-term flow assays by providing a reservoir for liquid to be used in the assay.

Figure 3B:
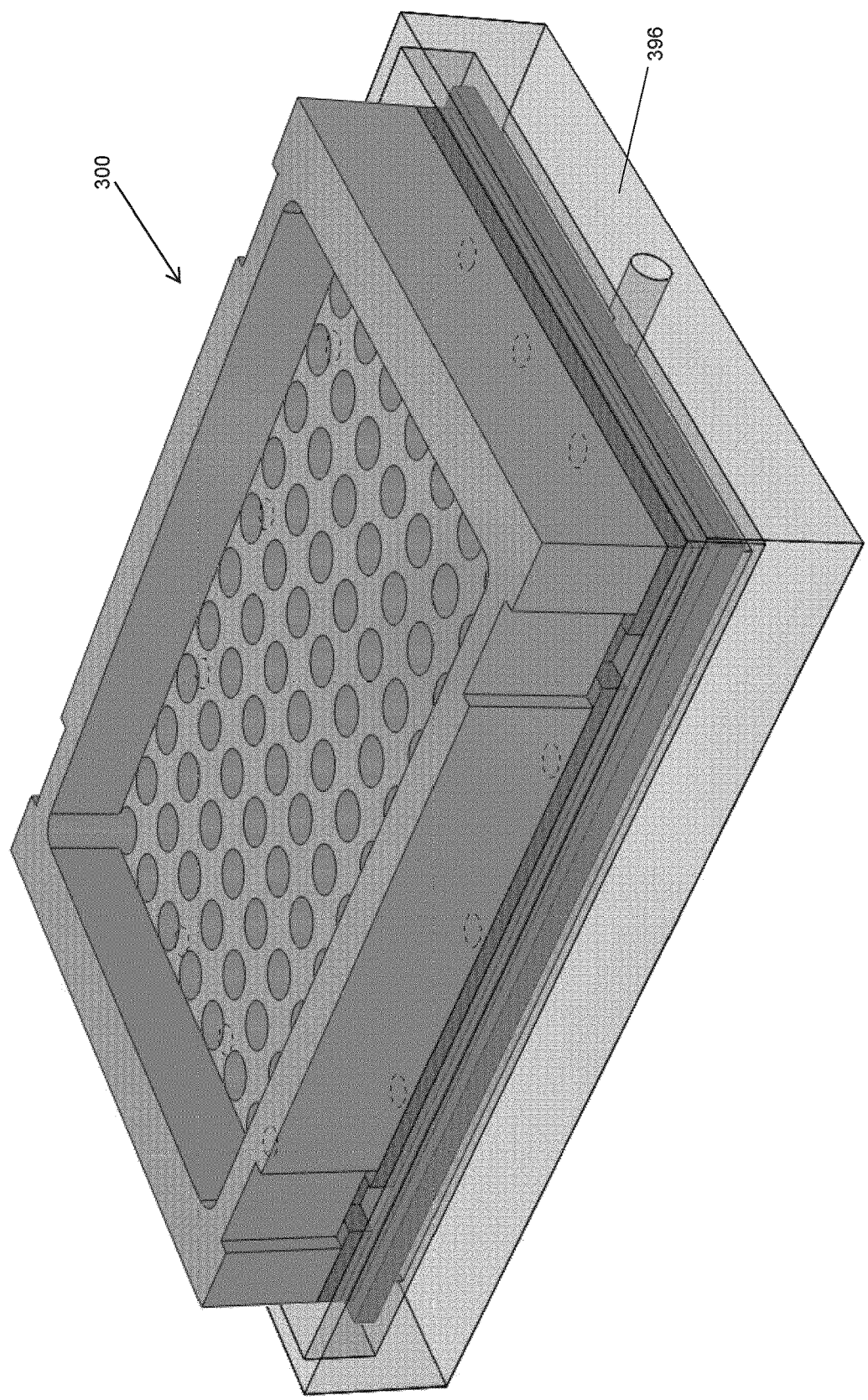
Figure 3C:
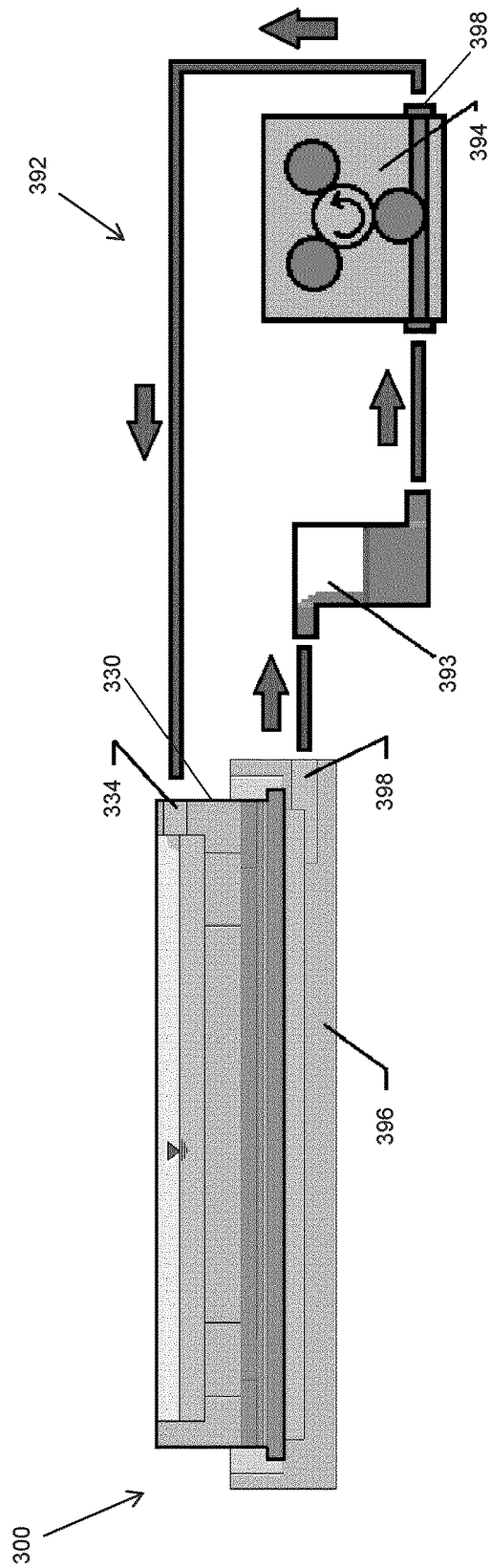

Referring to FIGS. 3b and 3c, which depict a perspective view of the assembled device (300) of FIG. 3a, wherein the assembled device (300) is coupled to a flow manifold (396) and a schematic side view of the assembled device (300) of FIG. 3b connected to a recirculatory flow assembly (392), the outlet of the flow manifold (398) is coupled to a damper (393), the damper (393) is coupled to a peristaltic pump (394), and the peristaltic pump (394) is coupled to an inlet (334) in the well block top to facilitate re-circulatory flow of liquid through the assembly (392) (arrows indicate direction of flow). By connecting the pump's outlet (398) back into the pool well block top (330), the fluid that passes through the recirculatory flow assembly (392) can be recirculated indefinitely.

Perfusion Configuration

In one embodiment of a microfluidic device provided herein, the device is configured for use in a perfusion assay or cell culture system. Perfusion assays may be designed to mimic the physiological conditions of blood flow in vasculature for an extended period of time. A perfusion flow configuration may be provided to a flow configuration of the microfluidic device provided herein, wherein the device comprises (top to bottom): a well block top, well block bottom, first cell culture layer (porous flow chamber), second cell culture layer (static chamber) and base block. In operation, seals, e.g., gaskets, are provided between the layers to maintain a liquid tight seal.

In operation, the assembled device is coupled to a flow manifold or and a perfusion assembly. Cells may be provided in one or more of the microchannels in a porous flow cell culture layer and optionally in one or more of the static cell culture chamber wells in a static cell culture layer. Fluid flow is induced in the porous flow chamber, either continuously or periodically, which facilitates transfer of molecules, nutrients, reagents, gasses, cell metabolites etc. through the porous membrane of the porous flow cell culture layer, thereby creating perfusion cell culture conditions.

Static Culture and/or Imaging Configuration

FIG. 4 depicts one embodiment of a microfluidic device provided herein, wherein the device (400) is configured for use in a static cell assay and/or cell culture system, the system having 2D (a-d), 3D (e) or 2D or 3D (f) culture conditions, wherein the device (400) is configured for use with an imaging device. This configuration enables users to culture cells under static (i.e., no flow) conditions and/or image cells housed by the cell culture microchannels and/or chamber using an external imaging device.

Figure 4A:
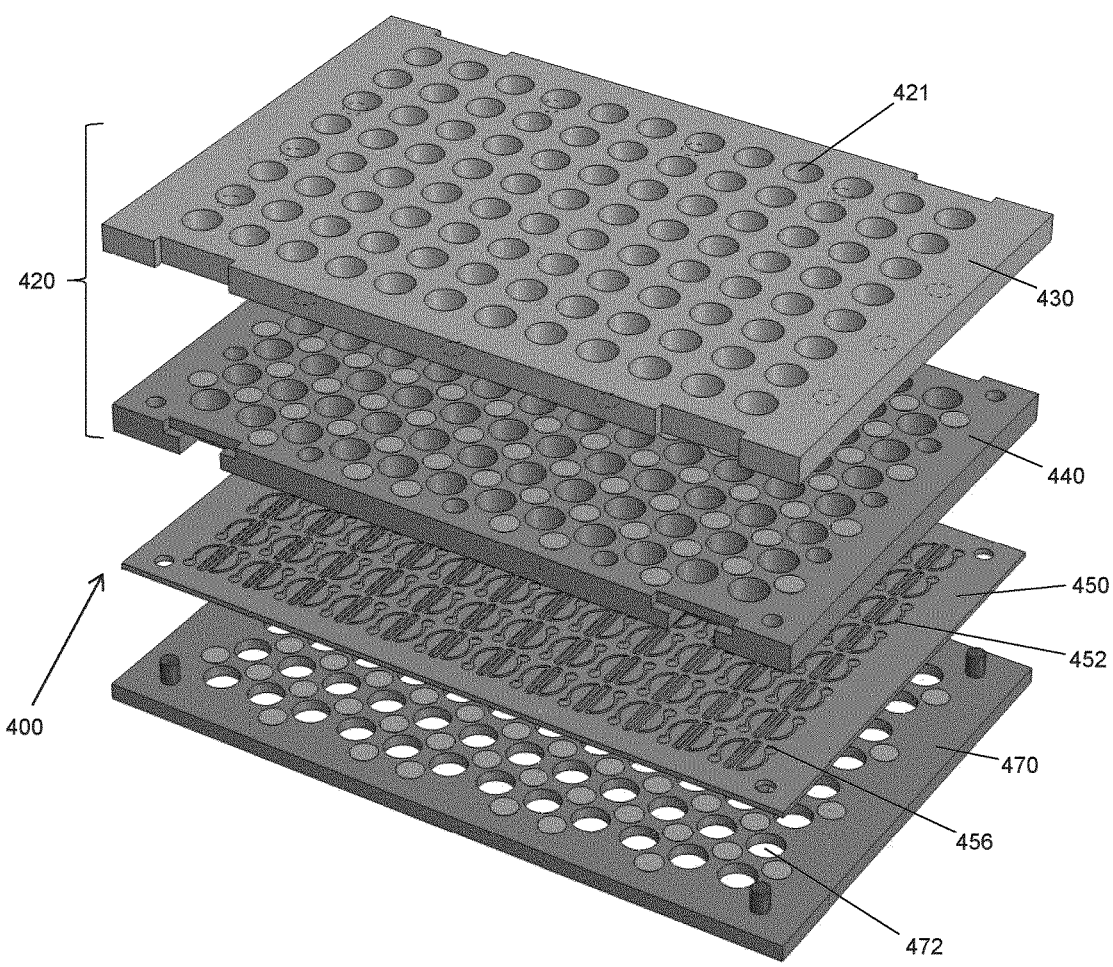
FIGS. 4a-f depict embodiments of a microfluidic device provided herein, wherein the device is configured for use in a static cell assay or cell culture system having 2D (a-d), 3D (e) or 2D or 3D (f) culture conditions and/or for use with an imaging device.
Figure 4B:
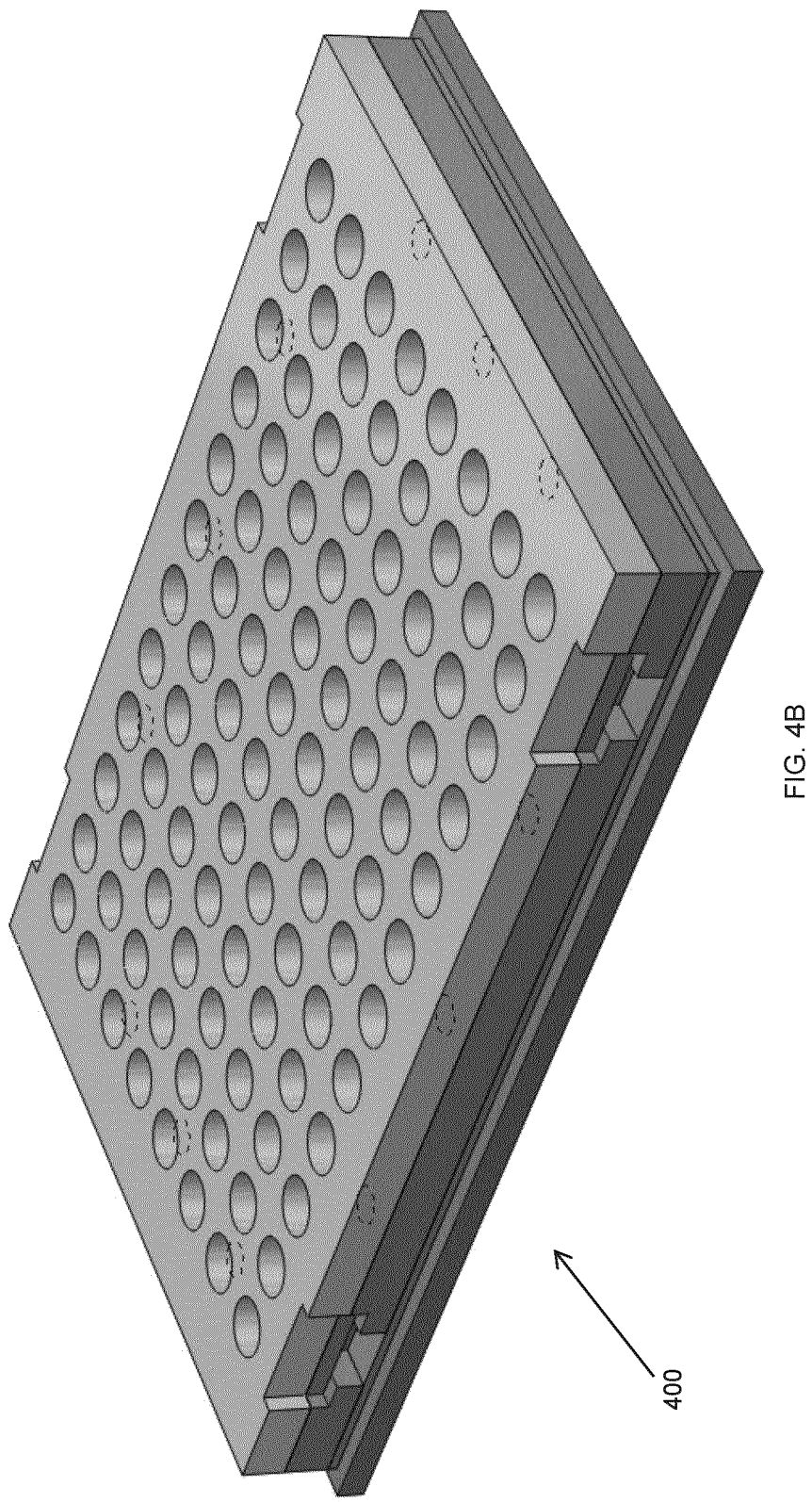
Figure 4C:
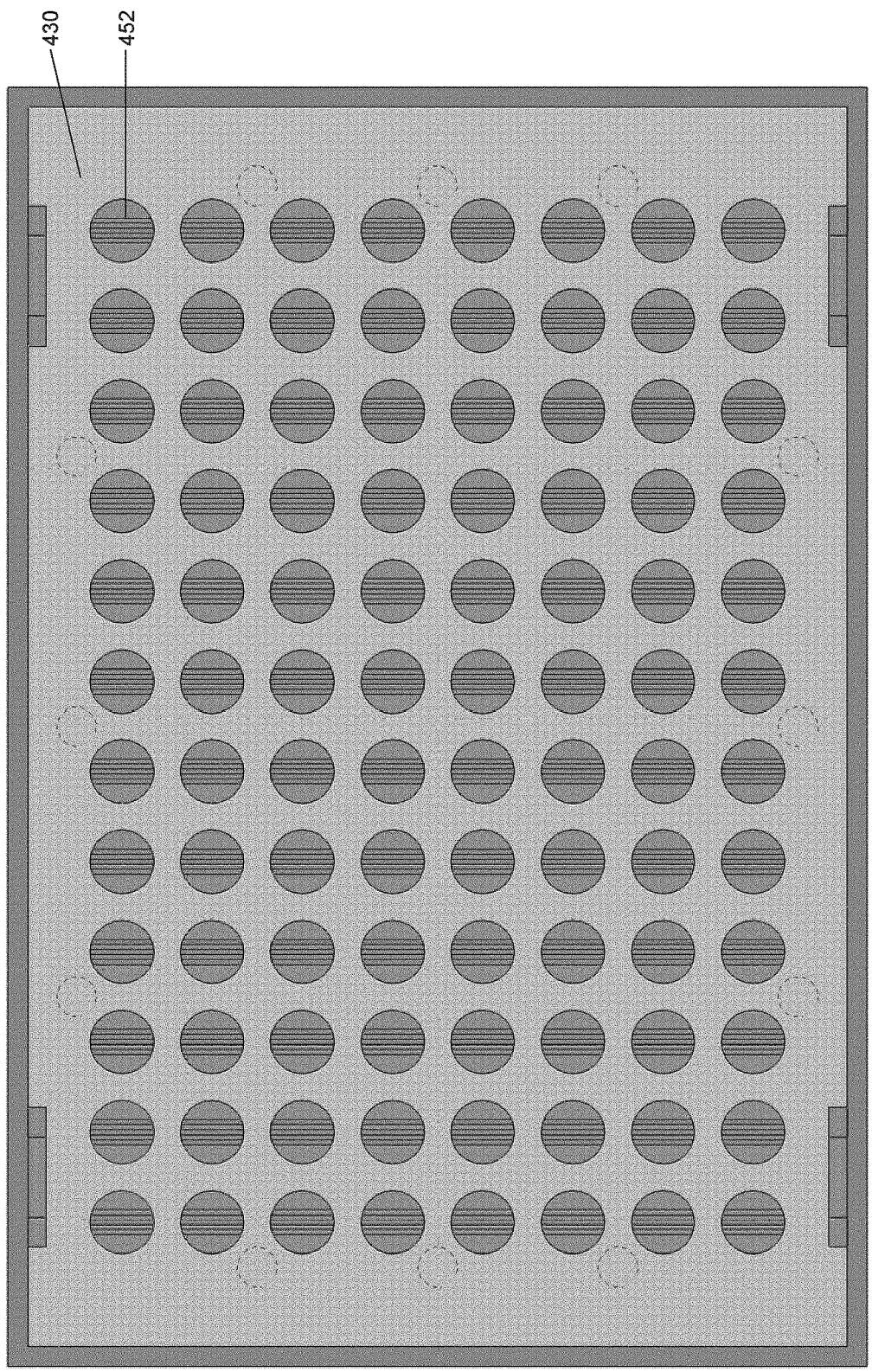
Figure 4D:
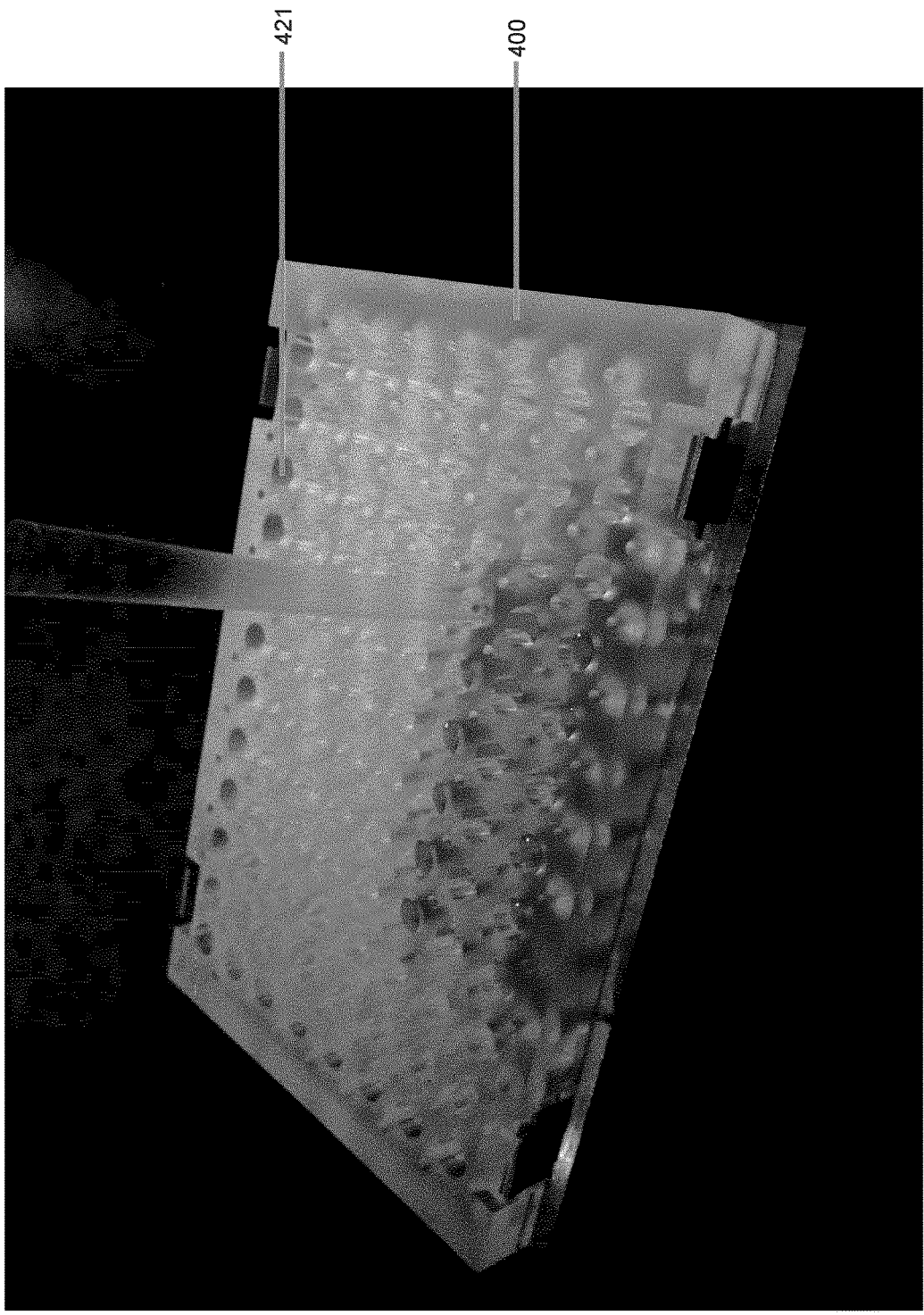

Referring to FIG. 4a, which depicts an exploded view of one embodiment of the microfluidic device (400) comprising four layers and configured for 2D culture: (from top to bottom) a well block top (430), a well block bottom (440), a cell culture layer (450) and an imaging base block (470). In operation, seals (not shown) would be provided between the well block (420) and cell culture (450) and the base block (470) to maintain a liquid tight seal. Unlike the flow configurations of the device, liquid from the well block (420) and cell culture layer (450) does not come into contact with the imaging base block (470). Rather, a seal is provided over the outlet (456) of the cell culture layer (450) to prohibit liquid contact with the imaging base block (470). Unlike the base block used in flow configurations of the device (e.g., 170), the imaging base block (470) provides optical access to each well (421) and corresponding portions of the cell culture layer (450). For example, optical access may be provided by providing apertures (472) in the imaging base block (470) that correspond with each well (421) in the well block (420) layer or by providing in the bottom surface of the imaging base block a material that may be imaged through (not shown). In one embodiment, the well block (420) is configured to allow open access to chambers in the cell culture layer (450), thereby allowing a user to directly add liquid, cells, hydrogels etc. into the microchannels (452) and/or static cell culture chamber wells (not shown) of the first (450) and second (not shown) cell culture layers, respectively.

Figure 4E:
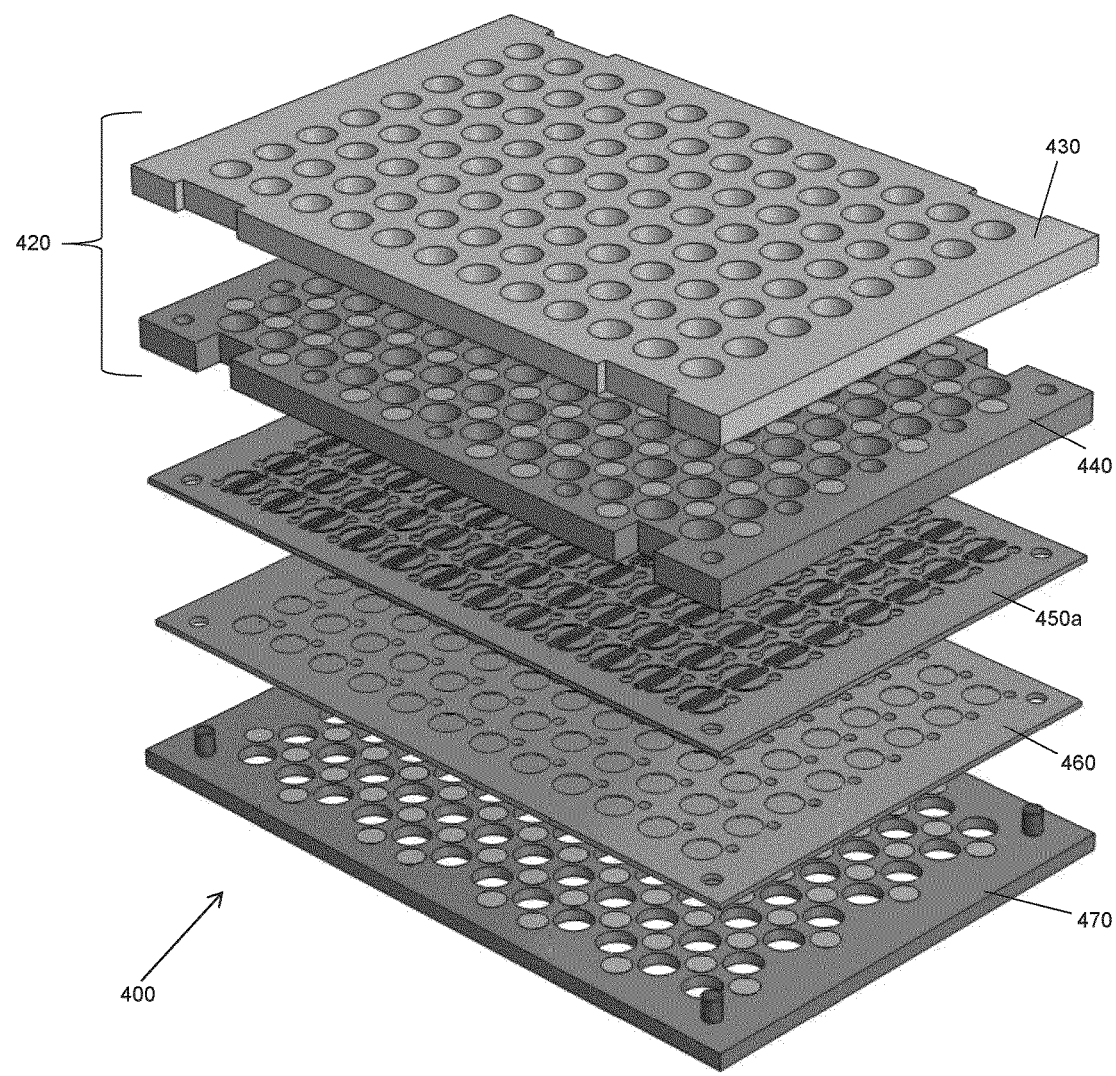
Figure 4F:
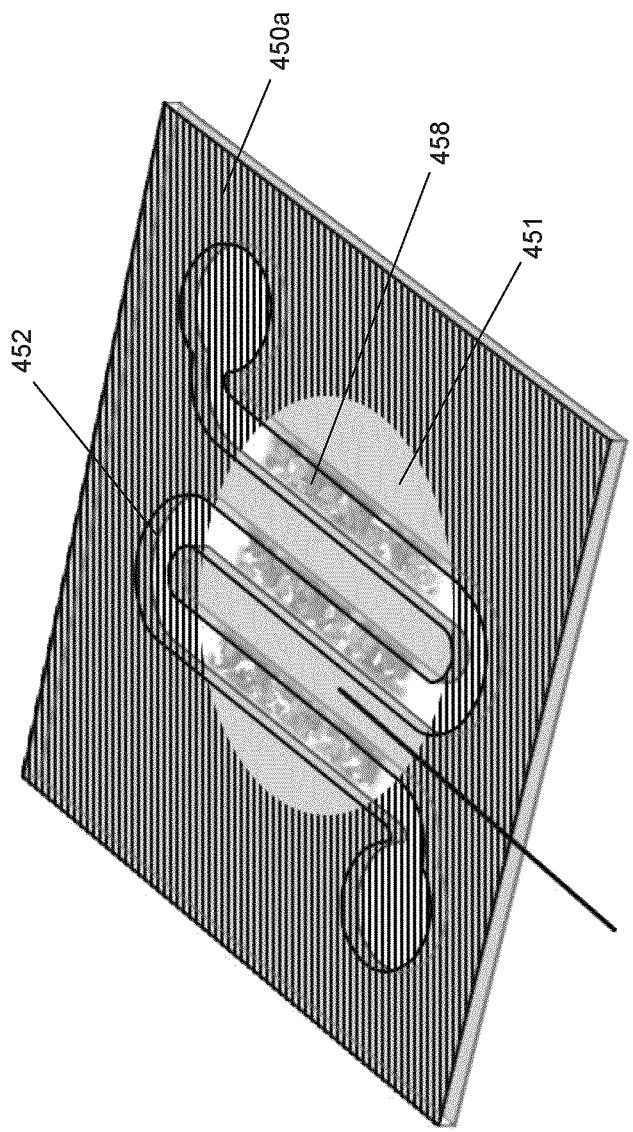

Referring to FIG. 4e, which depicts an exploded view of one embodiment of the microfluidic device, the device (400a) has five layers and is configured for 3D culture: (from top to bottom) a well block top (430), a well block bottom (440), a first cell culture layer (450a) (i.e., porous flow cell culture layer), a second cell culture layer (460) (i.e., a static cell culture layer) and an imaging base block (470). In operation, seals (not shown) would be provided between the well block (420) and first cell culture layer (450a) and the second cell culture layer (460) and the imaging base block (470) to maintain a liquid tight seal. A thin PDMS layer (not shown) may be provided between the cell culture layers (450a, 460) to provide a seal there between. FIG. 4f depicts a perspective view of a portion of the first cell culture layer (450a) of 4e, wherein the cells (458) are provided in the microchannel (452) of the first cell culture layer (450a) (i.e., a porous flow cell culture layer). The area shown in the light circle (451) corresponds to the portion of the first cell culture layer (450) that would be visible if a well (421) of the device (400) were imaged from below the base block (470).

The imaging configuration of the device (400) allows robotic equipment to interact with and use the microfluidic device (400), which further increases the device's (400) ease of integration into drug discovery screening and testing applications.

Each module category of the microfluidic device provided herein is further described below.

Well Block

FIG. 5 depicts embodiments of a well blocks of the microfluidic device provided herein. The well blocks function as a reservoir for reagents, suspended cells and/or other fluids provided in the well blocks. In various embodiments, the well block is the top layer in the assembled microfluidic device. Thus, in one embodiment, the well block, along with a base block, function together to hold the layers of the device together by providing substrates for clamping one or more layers therebetween.

In one embodiment, the configuration of the well block follows ANSI/SLAS microplate standards for well size and spacing, making the well block, along with the entire microfluidic device, compatible with standard liquid handling equipment (e.g., pipettes, robotics, etc.).

In one embodiment, the well block contains a plurality of microwells.

In one embodiment, the well block consists of two parts. In one embodiment, a top layer of the well block is machined from polyether ether ketone (PEEK), poly(methyl methacrylate) (PMMA; acrylic) or polytetrafluoroethylene (Teflon) and a bottom layer of the well block is machined from stainless steel, for example, 400 series stainless steel, which is magnetic. Well blocks machined from PEEK may be autoclavable. In one embodiment, the stainless steel bottom well block comprises a plurality of microwells and an array of magnetic disks, which are used to generate adequate clamping force between the well block and the base block to couple the microfluidic device for use under assay and/or cell culture conditions. In a preferred embodiment, the upper well block provides the well block with additional thickness, which facilitates increases in well volume with a minimal increase in weight of the microfluidic device. In a preferred embodiment, the top well block layer is about 3/16" to 1¼" thick and the bottom well block layer may be a thickness of about ⅛" to 3/16" thick.

In one embodiment, mating parts are used to align the modules of the microfluidic device. For example corresponding convex domes and concave craters depicted on the well block bottom and top, respectively, and corresponding pegs and receiving apertures depicted on the base block and cell culture layers respectively.

Figure 5A:
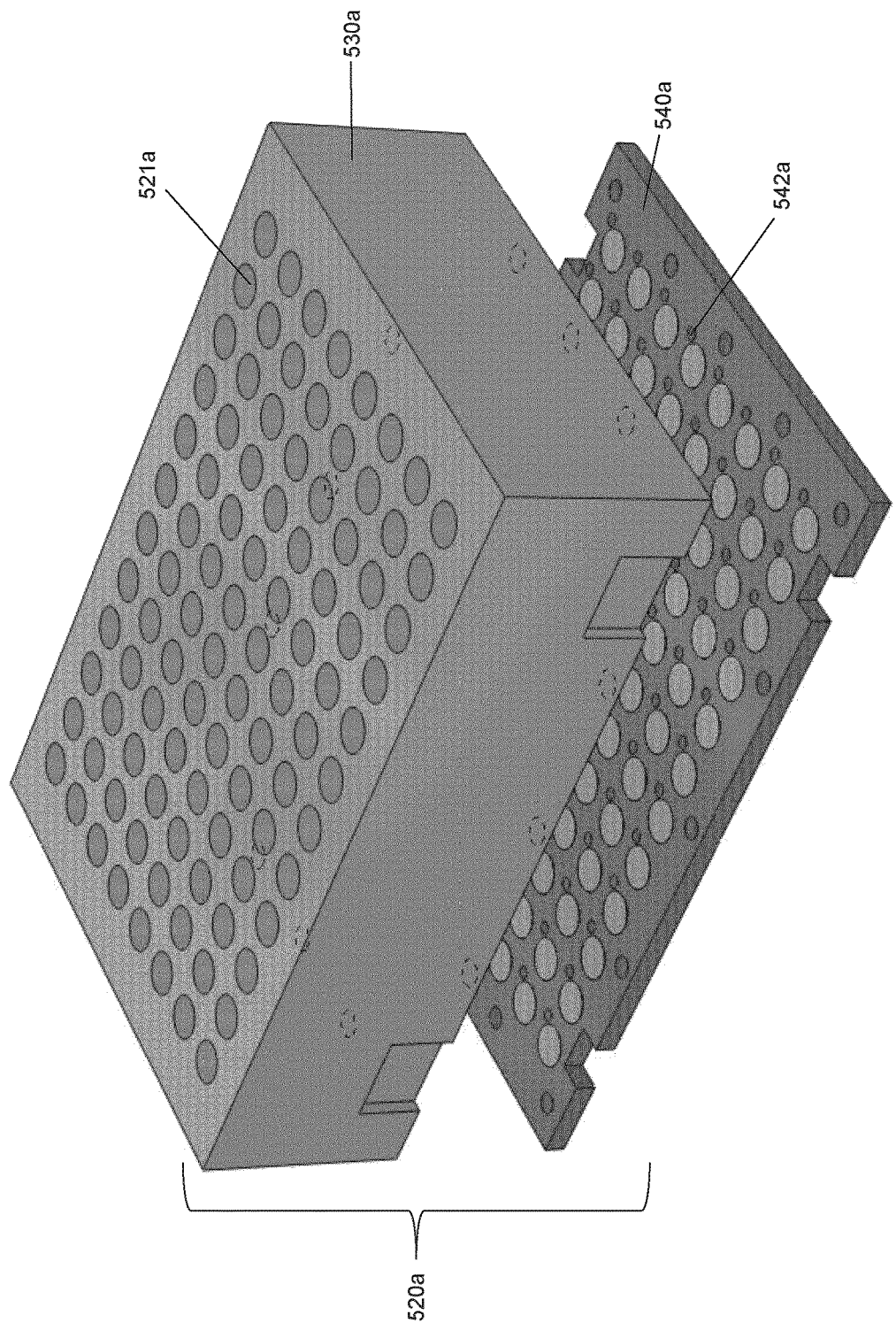
FIGS. 5a-c depict exploded perspective views of embodiments of the well block top and bottom of a microfluidic device provided herein.

Referring to FIG. 5a, which depicts an exploded perspective view of a "deep" well block top (530a) and a deep well block bottom (540a), in one embodiment, the deep well block (520a) contains 96 separate deep wells (521a), each deep well (521a) having a 1.5 mL capacity.

In one embodiment, each deep well (521a) in the deep well block top (530a) comprises an inner surface having a bottom portion comprising a first aperture (not shown), the first aperture aligning at least in part with a second corresponding aperture (542a) in the deep well block bottom (540a). The first and second (542a) apertures allow fluid communication between the deep well block top (530a) and deep well block bottom (540a).

Deep well blocks (520a) having 6, 12, 24, 48, 384 or 1536 deep wells (521a) may also be used in the microfluidic device provided herein, depending on the desired cell assay and/or culture environment. In one embodiment, the deep well block (520a) is suitable for use in relatively long-term experiments, for example up to 3 hours at 1 Pa sheer stress and 1.5 mL fluid volume or proportionally longer at lower shear stress/flow rate.

Figure 5B:
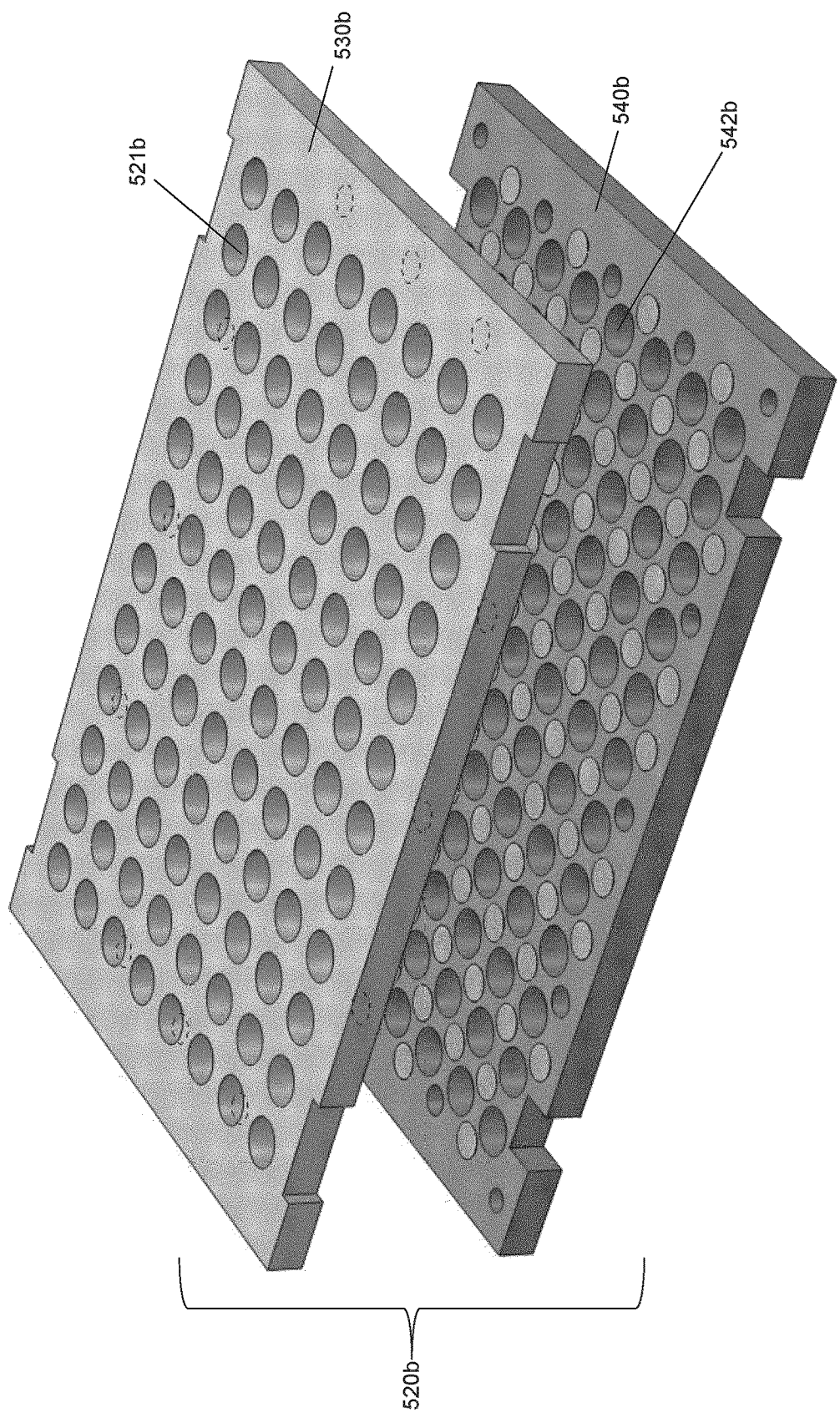

Referring to FIG. 5b, which depicts an exploded perspective view of a "shallow" well block top (530b) and a shallow well block bottom (540b), in one embodiment, the shallow well block (520b) is similar to the deep well block (520a) but has a relatively shallower or less thick profile. In one embodiment, the shallow well block (520b) contains 96 separate shallow wells (521b), each shallow well (521b) having a 0.25 mL capacity.

In one embodiment, each shallow well (521b) in the shallow well block top (530b) is bottomless, the bottomless portion of each shallow well aligning with a first aperture (542b) in the shallow well block bottom (540a). The bottomless portion of each shallow well (521b) and the first aperture (542b) in the shallow well block bottom allows: (i) fluid communication between the shallow well block top (530b) and shallow well block bottom (540b); (ii) a user to seed cells in a cell culture layer that may be disposed below the shallow well block (520b) via each shallow well (521b); and (iii) optical imaging of cells cultured in a device comprising the shallow well top (520b).

Like the deep well block (520a), shallow well blocks (520b) having 6, 12, 24, 48, 384 or 1536 shallow wells (521b) may also be used in the microfluidic device provided herein, depending on the desired cell assay and/or culture environment. In one embodiment, the shallow well block (520b) is suitable for one or more of seeding cells into microchannels and/or static cell culture chamber wells of a cell culture layer, embedding hydrogels in a static cell culture chamber well of a cell culture layer and imaging the contents of each shallow well (521b). The shallow well block (520b) is designed to allow a fully assembled microfluidic device to be used with automated imaging systems, such as microplate readers and high content imaging systems.

Figure 5C:
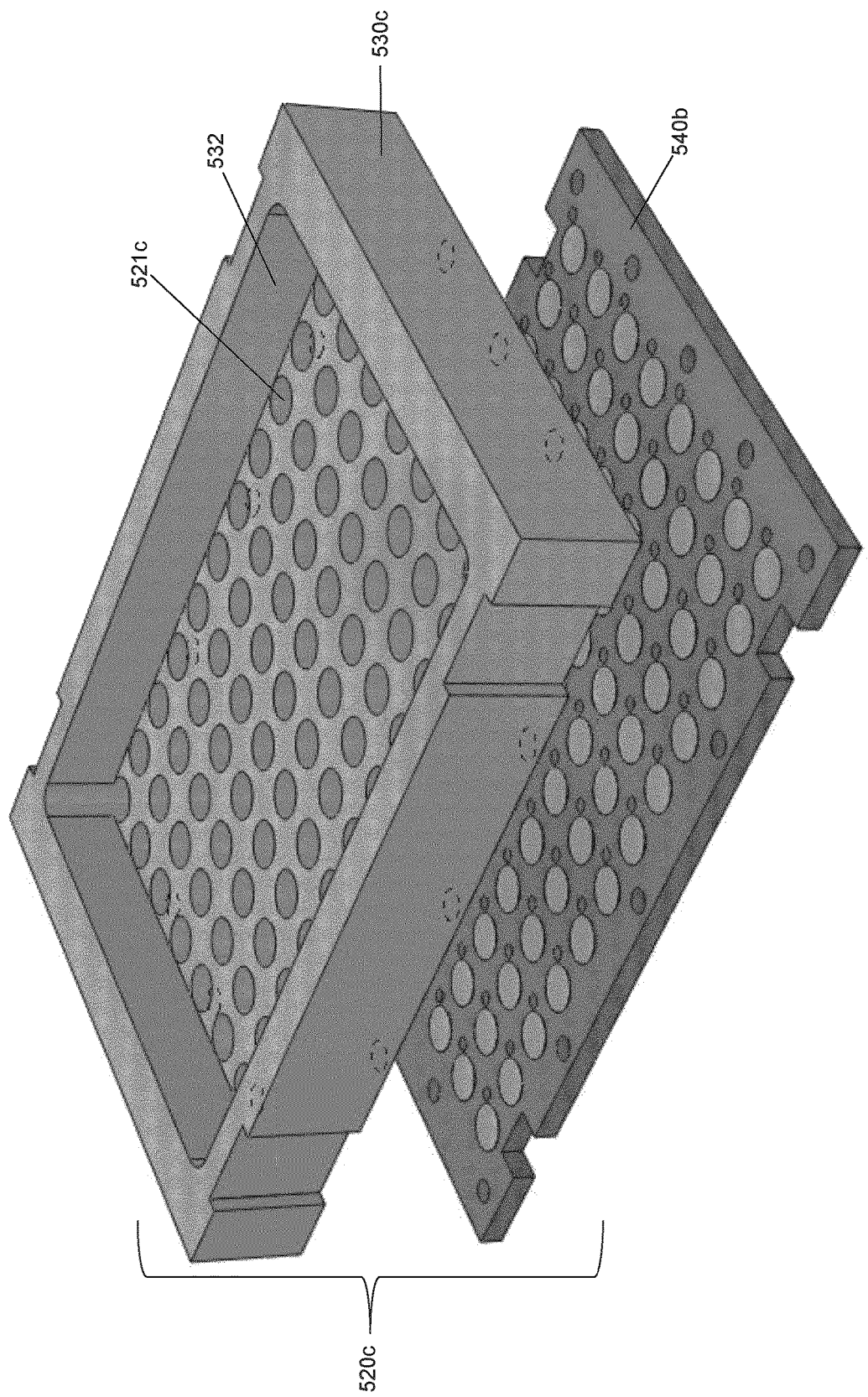

Referring to FIG. 5c, which depicts an exploded perspective view of a pool well block top (530c) and a well bottom (540), in one embodiment, the pool well block (520c) contains a large bottomless tray (532) that acts as a reservoir for pooling all reagents above a plurality of wells (521c) in the pool well block (520c). For example, a pool well block (520c) may have a capacity of about 100 mL to 500 mL, preferably about 150 mL. In one embodiment, the pool well block (520c) contains an inlet (not shown) suitable for coupling to a pump (not shown), allowing a pump to input liquid into the pool well block (520c). In preferred embodiments, the pool well block (520c) is suitable for use in long-term flow assays, such as, for example, recirculatory flow assays, which may be run indefinitely or with periodic replacement of fluids.

Cell Culture Layer

FIG. 6 depicts embodiments of a cell culture layer of the microfluidic device provided herein. In one embodiment, cell culture layers are single-use (i.e., a consumable product) modules fabricated from polycarbonate or polystyrene by laser cutting or hot-embossing, respectively, and oxygen plasma-treatment to improve hydrophilicity and cell adhesion compatibility of the material. In one embodiment, the cell culture layer is fabricated from PVC or PTFE sheets (e.g., about 100 μm thick) with adhesive backing and the plurality of flow chambers are laser cut in the sheet. In one embodiment, the cell culture layer may be adhered to a porous membrane via the adhesive backing on the cell culture layer. It is contemplated that cell culture layer may also be treated to improve material compatibility with cells. For example, coating the plastic surface of a cell culture layer, or part thereof, with extracellular matrix (e.g., collagen and/or fibronectin) may improve cell adhesion. In one embodiment, the cell culture layer may be adhered to a porous membrane comprising electrodes. It is contemplated that cells may be cultured on the electrodes of the porous membrane, such that a user may monitor the integrity of a cultured endothelial layer, for example, via electric cell-substrate impedance sensing (ECIS).

Figure 6A:
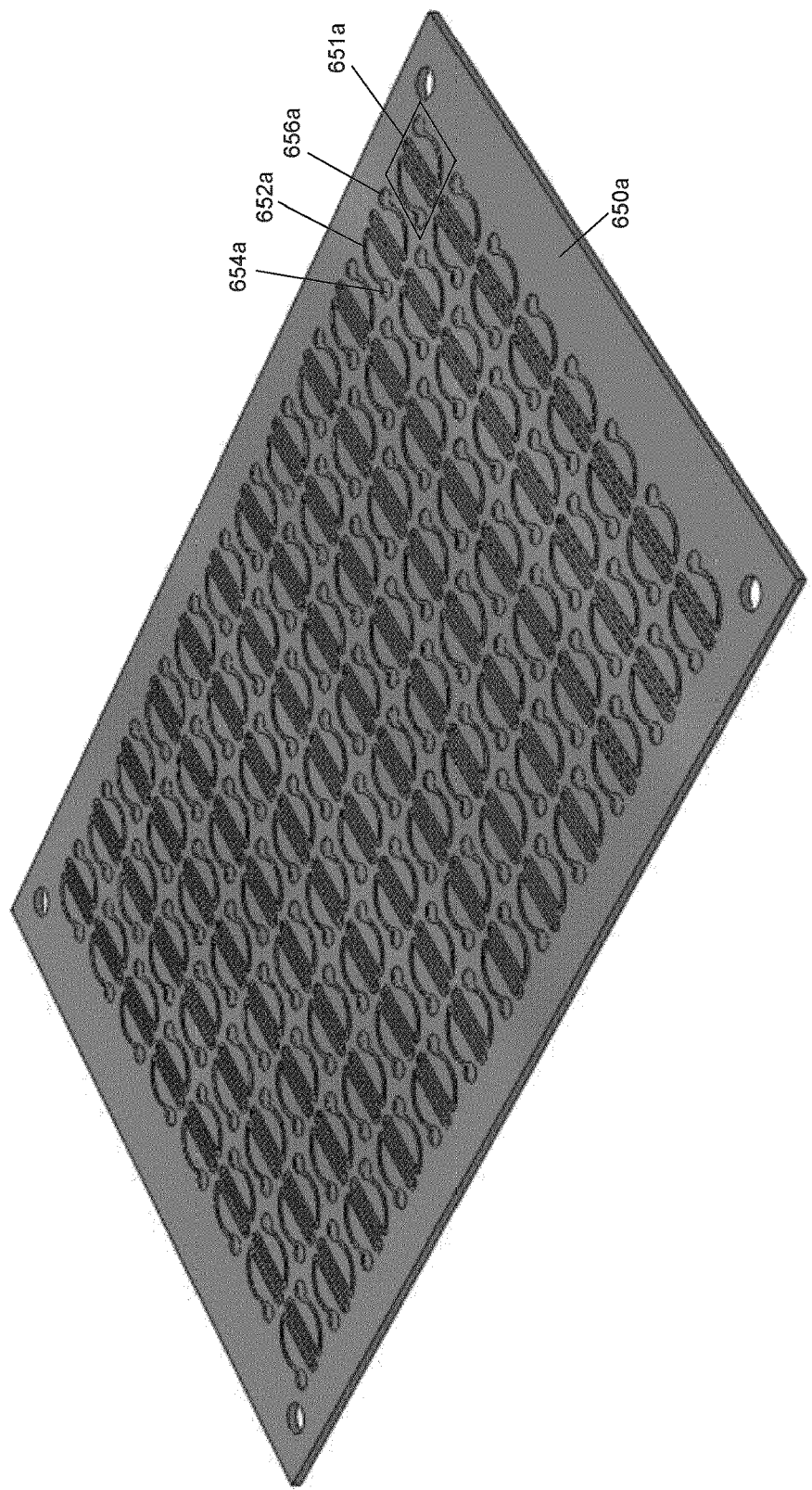

Referring to FIG. 6a, which depicts a cell culture layer (650a) comprising a plurality of flow chambers (651a), in one embodiment, the flow chamber cell culture layer (650a) has 96 separate microchannels (652a), each microchannel (652a) having an inlet (654a) and an outlet (656a) and a bottom surface having two walls extending upwards therefrom, the bottom surface and walls extending between the inlet (654a) and the outlet (656a). For example, a lateral cross-section of microchannels (652a) in a flow chamber cell culture layer (650a) may be "U-shaped". Each microchannel (652a) in a single flow chamber (651a) in the flow chamber cell culture layer (650a) corresponds to and is configured for fluid communication with a single well in a well block.

In one embodiment, cells are seeded, and optionally grown, on the bottom surface of each microchannel (652a) in a flow chamber (651a) of the flow chamber cell culture layer (650a). During a flow assay, the cells seeded on the bottom of each microchannel (652a) are exposed to shear stress induced by the active flow of fluid (e.g., media, reagents, drug candidates, etc.) passing over them. In one embodiment, microchannel (652a) height may be about 30-200 μm. The height of the microchannels (652a) may be selected to achieve a desired range of physiologically-relevant blood flow-induced shear stresses.

In one embodiment, shape and configuration of the microchannels (652a) in the flow chamber cell culture layer (650a) are designed to provide a surface area for cell growth, wherein the cells may be exposed to a constant rate of flow and shear stress. For example, the microchannel (152) depicted in FIG. 1c depicts a microchannel (152) having an elongated serpentine shape, wherein cells (158) are seeded in longitudinally extended sections (159a) of the microchannel (152) rather than in curved portions (159b) of the microchannel (152). In operation, the curved sections (159b) of the microchannel (152) may experience shear stresses that differ from those in the longitudinally extended sections (159a). Thus, in a preferred embodiment, cells (158) are seeded only in the longitudinally extended sections (159a) of an elongated serpentine-shaped microchannel (152). In one embodiment, a removable mask may be added to the flow chamber cell culture layer (150) to substantially limit cell seeding to a particular area of the microchannel (152), such as, for example, the longitudinally extended sections (159a) of a serpentine-shaped microchannel (152).

Figure 6B:
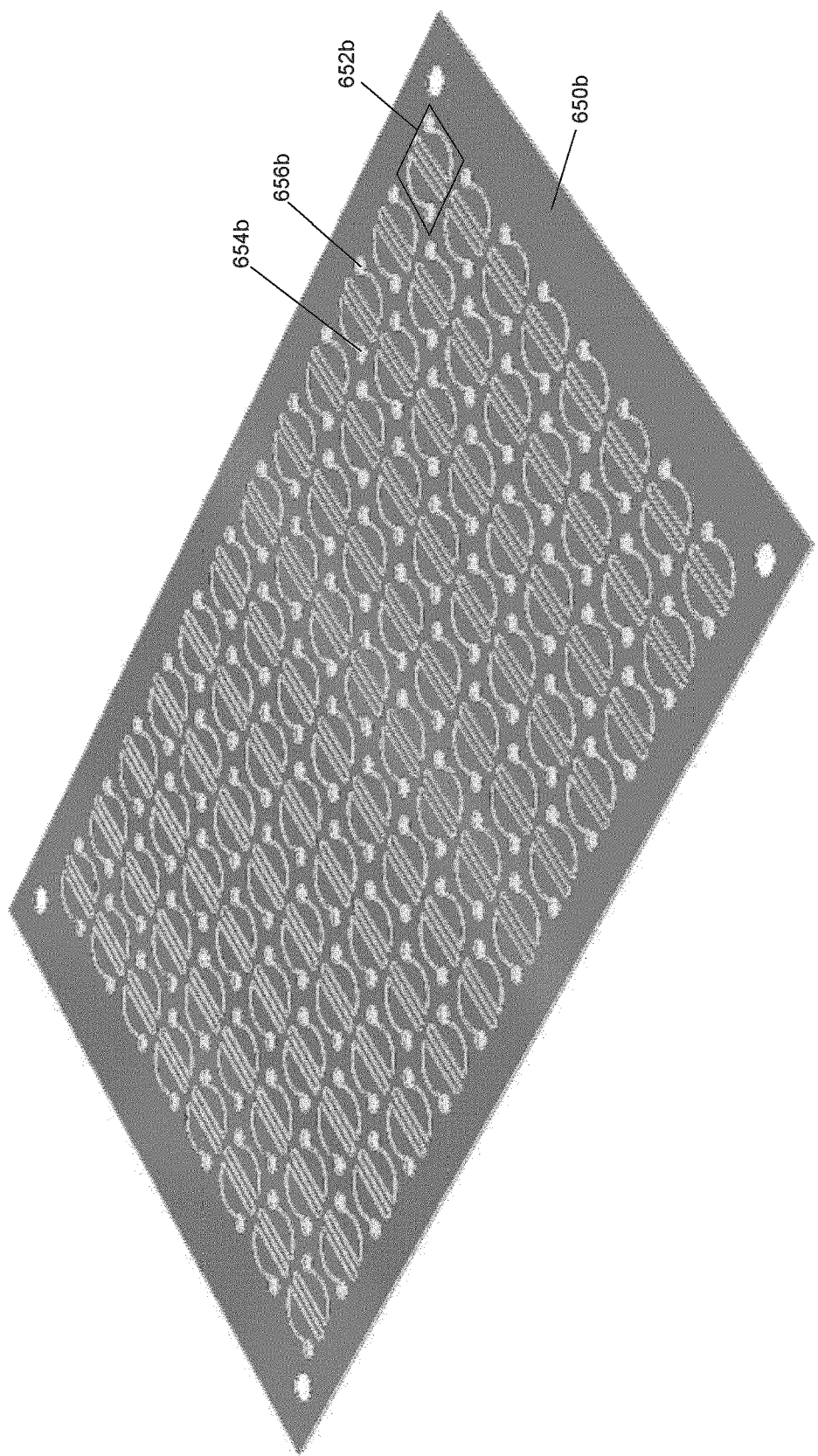

Referring to FIG. 6b, which depicts a "porous flow chamber" cell culture layer (650b) having 96 separate microchannels (652b) cut through a layer of material, each microchannel (652b) has an inlet (654b) and an outlet (656b) and a bottom surface of the microchannel (652b), which extends between the inlet (654b) and the outlet (656b). However, unlike the flow chambers (651a) in the flow chamber cell culture layer (650a), in each porous flow chamber (651b) of the porous flow chamber cell culture layer (650b), the bottom surface of the microchannel (652b) is provided by a porous, or semi-porous, membrane (shown in yellow in FIG. 6b) that is coupled to the bottom surface of the layer of material in which the microchannels (652b) are cut (e.g., coupling via adhesive). In other words, the microchannels (652b) cut through the porous flow chamber cell culture layer (650b) material are bottomless and the height of the material is equal to the height of the microchannels (652b). In one embodiment, the bottom surface of the microchannels (652b) in the porous flow chamber cell culture layer (650b) is provided by a polyethylene terephthalate (PET) semi-permeable membrane that is readily available commercially.

In one embodiment, the porous membrane (shown in yellow) enables cell-to-cell communication and/or cell migration between the microchannel (652b) and an underlying chamber (not shown). The underlying chamber is substantially shielded from fluid flow-induced forces acting on cells adhered to the membrane in the upper microchannel (652b).

Other microchannel shapes and configurations can be used in the flow chamber cell culture layer(s) (650a) and/or the porous flow chamber cell culture layer(s) (650b; 650d) of the microfluidic device provided herein. In one embodiment, the microchannel (652a, 652b, 652d) will be shaped and configured such that it maximizes surface area within an area for cell growth and/or adhesion. In one embodiment, the microchannel (652a, 652b, 652d) will be configured to allow for uniform and physiological shear stresses. Microchannels (652a, 652b, 652d) are configured to facilitate desired fluid transport. In one preferred embodiment, multiple flow chamber cell culture layers (650a) and/or porous flow chamber cell culture layers (650b; 650d) may be provided in a device.

Referring to FIG. 6d, which depicts a perspective view of a first cell culture layer (650d) disposed over a porous membrane comprising electrodes (655). Each microchannel (652d) has an inlet (654d) and an outlet (656d). The microchannel (652d) has a bottom surface, which is a portion of a top surface of the porous membrane comprising electrodes (655), which extends between the inlet (654d) and the outlet (656d). The porous membrane comprising electrodes 655 may be porous or semi-porous. It may comprise a metallic (conductive) pattern of electrodes for electric cell impedance sensing (ECIS). In one embodiment, ECIS can be applied to cells grown in the microchannels (652d) depicted in FIG. 6d. Each microchannel (652d), including bottom surface provided by the porous membrane comprising electrodes (655) comprises a 2 "cell" electrode pair, the electrode pair comprising an anode (667) and cathode (666) that is connected to a respective connector electrode pair. There is one connector cathode (668) for each cell cathode (666) and one connector anode (669) per 8 cell anodes (i.e., one connector anode (669) per row of microchannels (652). The connector electrodes (666, 667) serve as conductive pads to connect to a cable (e.g., a ribbon cable) that may then be connected to peripheral equipment (e.g., ECIS controller; voltage generator). A user may apply alternating current to one or more sets of electrodes (666, 667) and determine a range of electrical resistance (for a range of AC frequency), which a user may then correlate with one or more cell characteristic, such as, for example, cell confluency, permeability, density, function, etc.

In one embodiment, the porous membrane comprising electrodes (655) is coupled to the bottom surface of the layer of material in which the microchannels (652d) of the first cell culture layer are cut (e.g., coupling via adhesive).

In one embodiment, gold or chromium electrodes are printed on the porous membrane via vapour deposition.

It is contemplates that other configurations of electrodes may be applied to the porous membrane layer 655 in order to provide a substrate that is suitable for cell growth and subsequent analysis by ECIS.

Figure 6C:
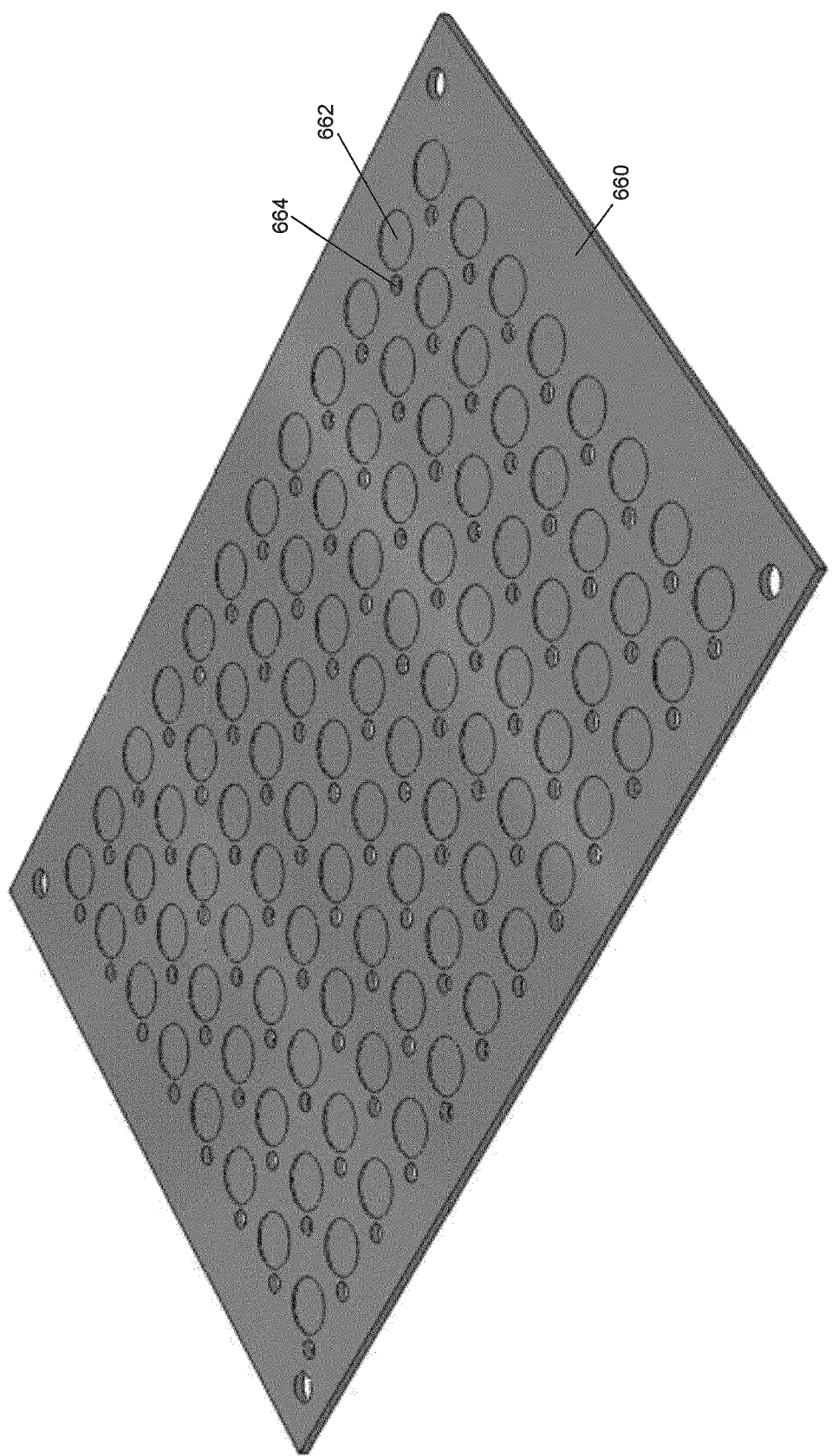

Referring to FIG. 6c, which depicts a static chamber cell culture layer (660), in one embodiment, the static chamber cell culture layer (660) has 96 separate cell culture chamber wells (662), each cell culture chamber well (662) having a corresponding outlet (664) configured for fluid communication with a base block and each chamber well (662) configured for fluid communication with one well in a well block. In one preferred embodiment, a plurality of flow chamber cell culture layers (650a), porous flow chamber cell culture layers (650b), and/or static chamber cell culture layers (660) may be provided in a device.

In one embodiment, the static chamber cell culture layer (660) is designed to house cells and/or biomaterials in one or more cell culture chamber wells (662), but under static conditions (no flow). In one embodiment, a static cell culture chamber well (662) is placed directly under a porous flow chamber (651*b*) to enable a 3D co-culture environment (i.e., allowing cell interaction between the two chambers (662 and 651*b*). This feature broadens the range of assays the device can be used to perform. In one embodiment, a 3D hydrogel comprising cells is provided into a static cell culture chamber well (662) of a static chamber cell culture layer (660).

In one embodiment, the static chamber cell culture layer (660) is fabricated by hot embossment of sheet PS, PMMA or PC, for example. In one embodiment, the embossed sheet may then be covered with a layer of PDMS, which functions as a gasket, providing adhesion between flow chamber and static chamber cell culture layers.

Fluid Collection Layer

Figure 8:
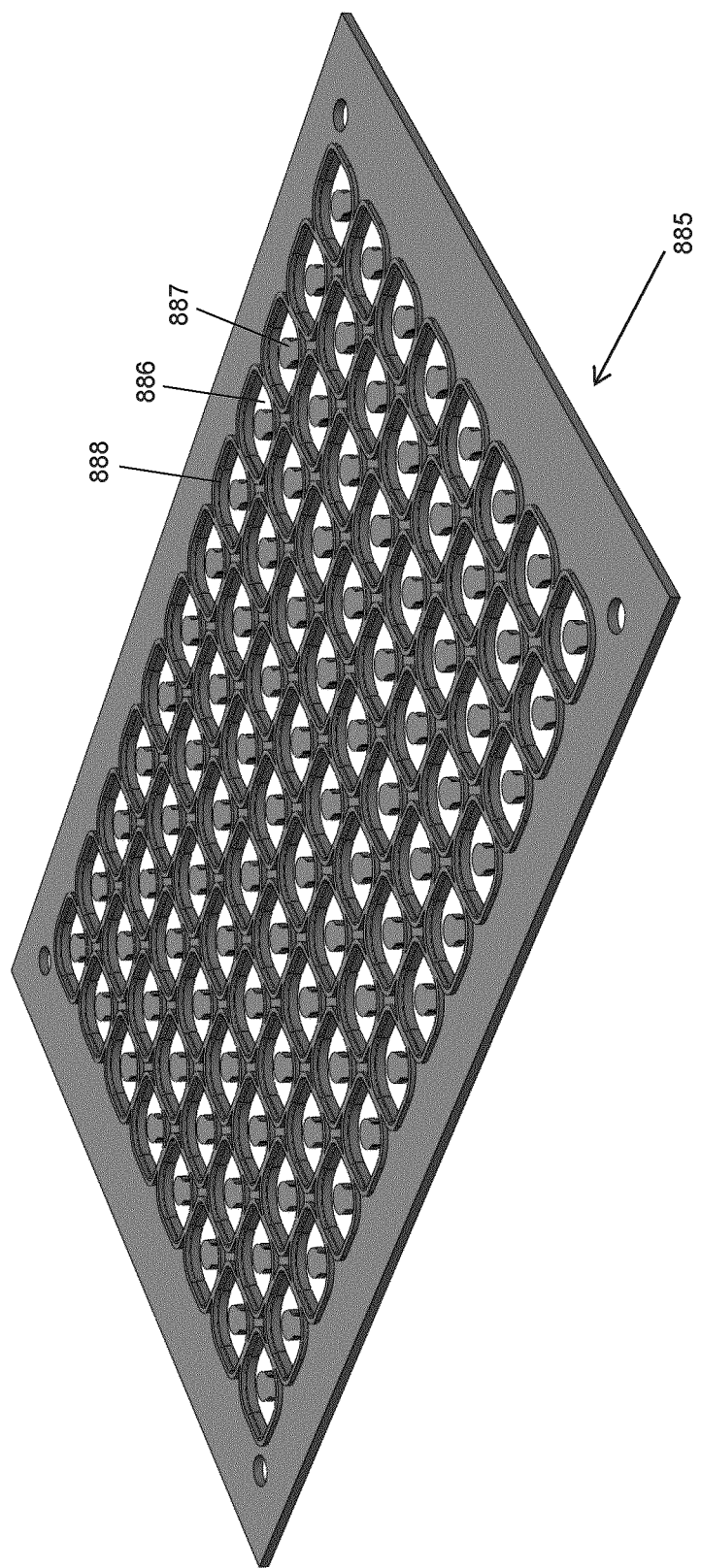
FIG. 8 depicts a perspective view of one embodiment of a fluid collection layer.

FIG. 8 depicts a perspective view of one embodiment of a fluid collection layer (885) of a microfluidic device provided herein. The fluid collection layer (885) functions to provide a plurality of bottomless fluid collection chambers (886), each corresponding to a flow chamber in the cell culture layer, for collecting effluent media from one or more flow culture chambers of the cell culture layer(s) of the microfluidic device. A bottom, for the fluid collection chambers (886) is provided by an upper surface of the base block, when the fluid collection layer and base block are aligned and coupled. In one embodiment, a fluid collection layer (885) comprises 96 bottomless fluid collection chambers (886), each bottomless chamber (886) being disposed in the fluid collection layer (885), such that it corresponds to one of the microchannels in a corresponding first cell culture layer and/or one of the static cell culture chamber wells of a corresponding second cell culture layer when a first cell culture layer and/or a second cell culture layer and the fluid collection layer (885) are coupled together. In one preferred embodiment, each bottomless fluid collection chamber (886) is configured to house a volume of up to about 50 uL. In one embodiment, each bottomless chamber (886) comprises at least one wall (888) defining an internal space of the bottomless chamber (886). In one embodiment, each bottomless chamber (886) comprises at least one projection (887) extending from at least one wall (888) of the bottomless chamber (886) into the bottomless chamber (886), the projection (887) extending substantially in the plane of the fluid collection layer (885). In one embodiment, the projection (887) functions to maintain space in the bottomless chamber (886) when a second cell culture layer is disposed thereupon. In one embodiment, a bottom is provided to the bottomless fluid collection layer, by an upper surface of a base block coupled thereto.

Base Block

FIG. 7 depicts embodiments of a well block bottom of a microfluidic device provided herein. The base block functions to provide a bottom layer for the microfluidic device. In one embodiment, the base block provides a bottom substrate that cooperates with a well block (i.e., the top layer of the device) to clamp together layers of the device. In this embodiment, the bottom layer may comprise magnetic discs for clamping. In one embodiment, the base block is machined from stainless steel (e.g., 400 series stainless steel).

Figure 7A:
FIGS. 7a-d, depict perspective views of embodiments of the well block bottom of a microfluidic device provided herein.

Referring to FIG. 7*a*, which depicts a imaging base block (770*a*), in one embodiment, the imaging base block (770*a*) provides direct optical access to each well in the microfluidic device, which allows a user to image internal layers of the device. For example, optical access may be provided by providing apertures (772*a*) in the imaging base block (770*a*) that correspond with each well in a well block layer. In one embodiment, the imaging base block (770*a*) is fabricated to have the same base profile as a standard well plate, thereby permitting use of the assembled microfluidic device with conventional microplate readers. The imaging base block (770*a*) is also referred to as an "imaging" base block herein.

Figure 7B:
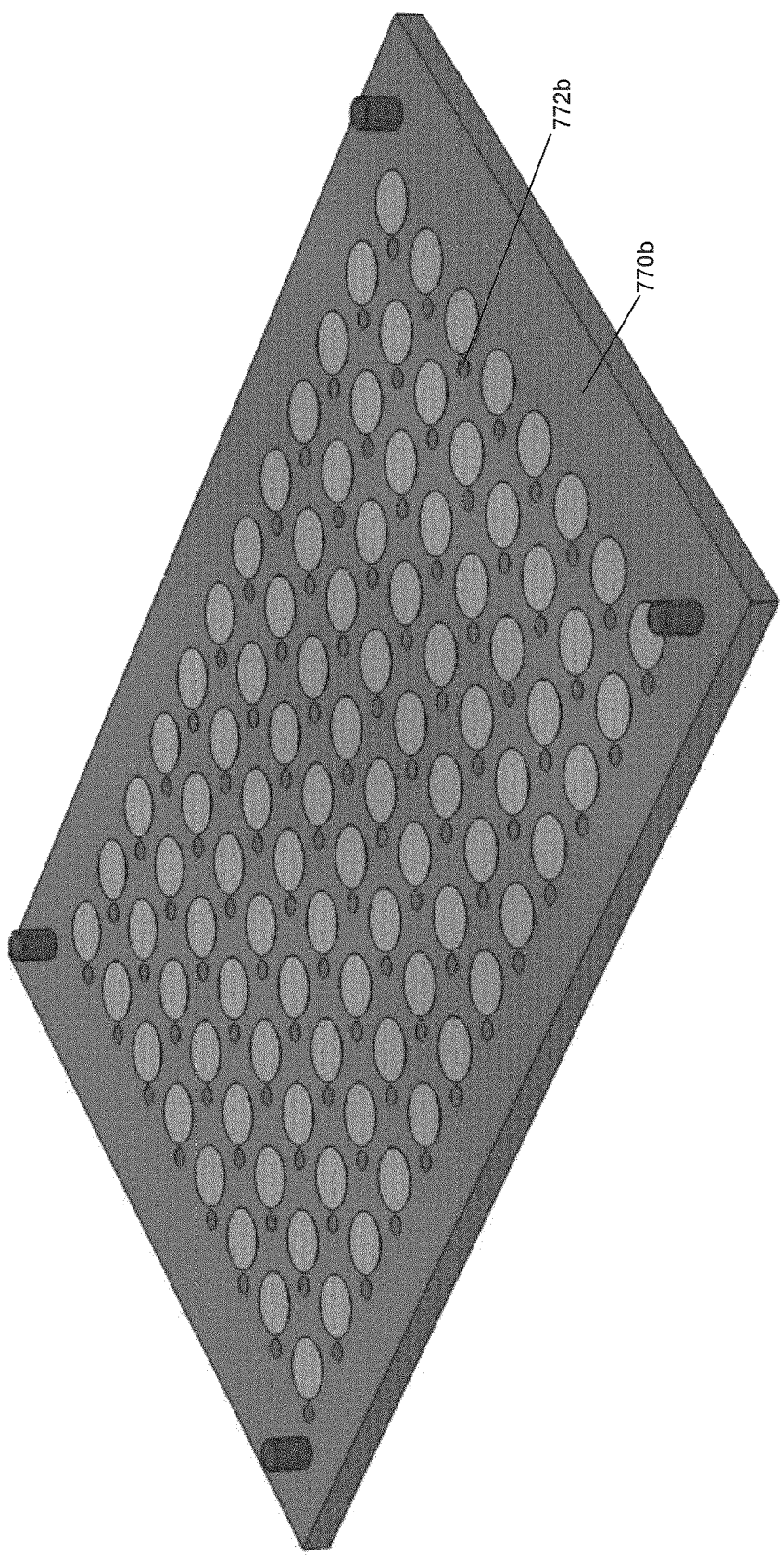

Referring to FIG. 7*b*, which depicts a flow base block (770*b*) that may be configured to communicate with vacuum or flow manifolds, this configuration allows the user to carry out flow-based assays using the microfluidic device. Unlike the imaging base block (770*a*), the flow base block (770*b*) does not have apertures (772*a*) that correspond with each well in a well block layer. Rather, the area (772*b*) of the flow base block (770*b*) corresponding with each well in a well block layer and each chamber in a cell culture layer is impermeable to fluid. In one embodiment, a flow base (770*b*) block may be configured for communication with one or more of the following components:

Flow manifold: A flow manifold is used to connect the assembled device to a pump. The flow manifold functions to drain fluids from the well block (through the microfluidic channels) at a constant flow-rate set by the pump.

Vacuum manifold: A vacuum manifold is used to generate flow via air pressure, rather than flow caused by movement of an incompressible fluid. It serves a function similar to a flow manifold.

Pressure regulator: A pressure regulator may be used in conjunction with a vacuum manifold to generate flow in the system. The pressure regulator can actively adjust the air pressure in the vacuum manifold, thereby creating a pressure gradient across the microfluidic channels, forcing fluid flow.

Pump: A pump may be attached to the device in order to move fluids through the system. The microfluidic device is compatible with various pump types, for example a peristaltic pump. A peristaltic pump allows a user to set a desired active flow-rate thereby enabling precise fluid force control.

For pump driven flow (peristaltic pump), the flow-rate is simply set by the pump speed, negating the need for a peripheral controller.

Flow damper: Flow dampers may be attached serially between the microfluidic device and a pump to stabilize flow rates in the system (e.g., remove pulsatile flow effects generated by a peristaltic pump).

Tubing: Tubing may be used to connect the microfluidic device to the pump and/or other external components to allow fluid to move to and from the device.

Figure 7C:
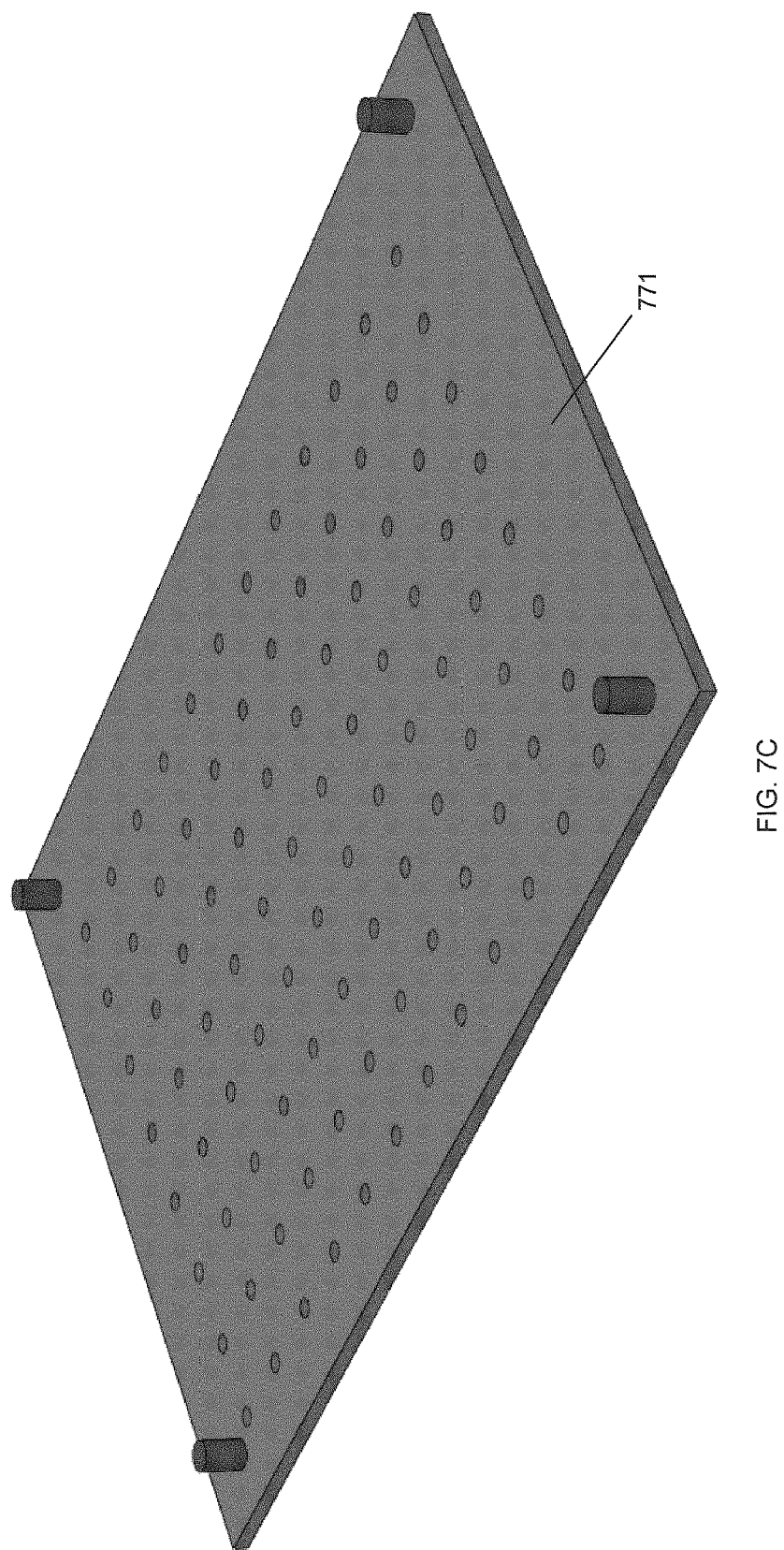
Figure 7D:
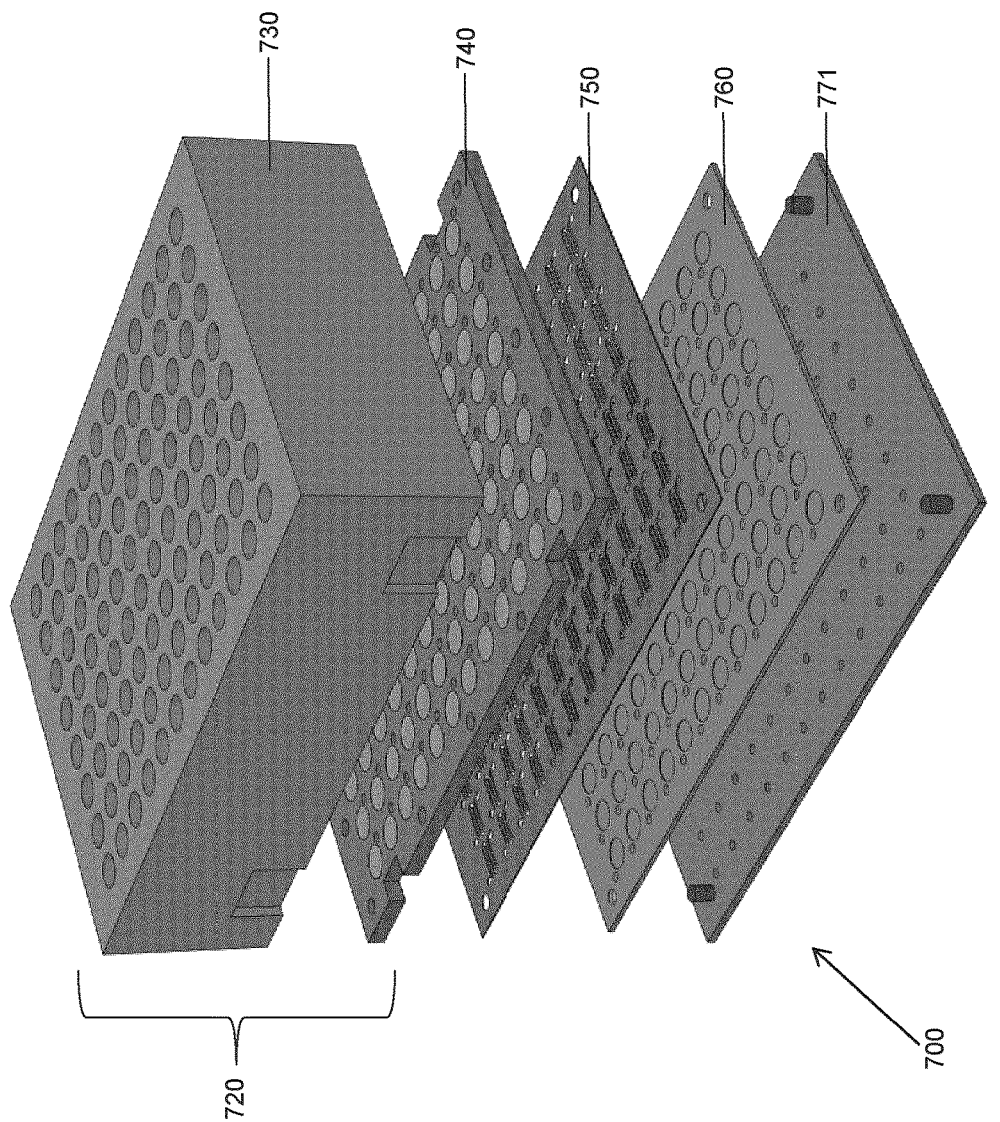

Referring to FIG. 7*c*, which depicts a flow base block (770*c*) that may be configured to communicate with vacuum or flow manifolds, this configuration differs from 770*b*, in that it lacks magnetic discs. In one embodiment, the flow base block (770*c*) is made of stainless steel (e.g., 400 series, which is magnetic). Referring to FIG. 7*d*, In one preferred embodiment, coupling of the modules provided is achieved using magnetic forces provided by well block magnetic discs (782*d*), and the composition of the material in the flow base block (770*d*).

In one embodiment, the imaging base block lacks magnetic discs (configuration not shown). In one preferred embodiment, coupling of the modules provided is achieved using magnetic forces provided by well block magnetic discs, and the composition of the material in the imaging base block lacking magnetic discs.

Flow Control Layer

Flow control layers act as flow-rate stabilizing modules and/or intermediate layers used to couple other modules.

Examples of flow control layers include: (i) Seals (e.g., gaskets), which may be provided in between layers (e.g., between a well block and a cell culture layer, between two cell culture layers, between a cell culture layer and a base block) to form waterproof seals and prevent leaks. Seals may be fabricated from silicon rubber or other materials, such as polyurethane, neoprene or polydimethyl siloxane. (ii) Filters, which function as flow resistors, allowing a user to vary the flow rates spatially across the device if desired. For example, if the user requires different flow rates across 96 wells, different filters may be provided between different wells in the device. Filter substrates may be cut from standard paper filters to fit the device. Commercially available or customs filters may be used with the microfluidic device provided herein. (iii) Protein filters, which function to capture proteins secreted by cells housed in the cell culture layer(s). Use of protein filters, such as, for example, nitrocellulose or polyvinylidene fluoride filters, in the microfluidic device provided herein allows a user to analyze the secretome of cells cultured/assayed in the device.

Kit

In one embodiment, a kit comprised of modular parts from which a user may assemble a microfluidic device for use in cell assays and/or cell culture is provided.

In one embodiment, the kit comprises: at least one well block, at least one cell culture layer, at least one base block and at least one flow control layer. The at least one well block may be a deep well block, a shallow well block, a pool well block or any combination thereof. The at least one cell culture layer may be a flow chamber cell culture layer, a porous flow chamber cell culture layer, a static chamber cell culture layer or any combination thereof. The porous flow chamber cell culture layer may comprise a porous membrane or a porous membrane comprising electrodes. The at least one base block may be a flow base block, an imaging base block or any combination thereof. The at least one flow control layer may be a seal (e.g., a gasket), a filter, a protein filter or any combination thereof. In one embodiment, the kit may further comprise a fluid collection layer. In various preferred embodiments, instructions for one or more of assembly, use and sterilization of the device are provided with the kit.

Methods of Use

In one embodiment, a method for culturing cells in the microfluidic device is provided. Cells or tissues may be cultured encapsulated in a hydrogel, other matrix, unencapsulated or on a scaffold. Any cell or tissue of interest may be cultured. For example a cell may be normal, mutant, cancerous or diseased. The cell may be derived from any unicellular organism (e.g., bacteria, protists) or multicellular organism (e.g., animal, plant, etc.). The tissue may be derived from any multicellular organism. The cultured cells or tissues may be a single cell or tissue type or a plurality of cell and/or tissue types. One or more cell or tissue types may be cultured simultaneously in the microfluidic device. A single cell or tissue type may be cultured separately in separate culture chamber wells, or more than one cell or tissue type may be cultured in a chamber.

In one embodiment, different types of cells or tissues representative of the body (e.g., human or mammalian) may be cultured, e.g., heart, kidney, liver, lung, heart, stomach, intestines, brain, neurons, glia, pancreas, ovary, muscle (skeletal, cardiac, smooth, etc.), skin, etc. Multiple cell or tissue types may be cultured in 2D or 3D configurations of the microfluidic device provided herein under flow or static (i.e., non-flow) conditions.

It is contemplated that various model systems may be developed using one or more embodiment of the device provided herein. For example, various endothelial and/or epithelial tissue systems may be modeled using one or more embodiment of the device provided herein, such as, but not limited to: vascular systems (i.e, tissue systems comprising an endothelial-vascular smooth muscle cell interface); valvular systems (i.e, tissue systems comprising an endothelial-valvular interstitial cell interface); cardiac systems (i.e, tissue systems comprising an endocardial-cardiomyocyte-fibroblast interface); gut systems (i.e, tissue systems comprising an intestinal epithelial-stromal cell interface); ocular systems (i.e, systems comprising a retinal epithelial-endothelial interface); cancer systems (i.e, tissue systems comprising metastatic cells and an endothelial parenchymal tissue interface); or Immunology systems (i.e, tissue systems comprising a blood cell-endothelial cell interface).

Some non-limiting examples of such model systems are provided below.

Liver Model System

For example, in one embodiment, the device provided herein is used to culture one or more cells relevant to a liver model system. In a preferred embodiment, the device suitable for use in the liver model system comprises at least five layers: (from top to bottom) a well block top, a well block bottom, a first cell culture layer (e.g., a layer comprising porous flow chambers), a second cell culture layer (e.g., a layer comprising static chambers), and a base block. Optionally, the device may further comprise a collection chamber layer. Optionally, the first cell culture layer may comprise a porous membrane comprising electrodes suitable for culture of cells thereon. A device comprising electrodes may be used, for example to measure one or more of: endothelial barrier function, endothelial ion channel activities, endothelial ligand binding and cell signaling, endothelial cell metabolism, endothelial cytotoxicity, adhesion of circulating cells to the endothelium, transendothelial migration of cells (such as immune cells, metastatic cells, circulating stem cells, pathogens, etc.), and transport of drugs and drug delivery vehicles across the endothelium.

For example, in one embodiment, liver sinusoidal endothelial cells are seeded in microchannels in the first cell culture layer, for example, onto a bottom surface of the microchannels. Preferably, the bottom surface of the microchannels (e.g., the porous membrane) is coated with one or more extra cellular matrix proteins. Natural (e.g., collagen I) or synthetic (e.g., polyethylene glycol) hydrogels embedded with hepatocytes are polymerized directly inside static cell culture chamber wells of the second cell culture layer. Optionally, other cells of interest (e.g., Kupffer cells) may be added to one or more static cell culture chamber wells. When the seeded first and second cell culture layers are coupled and cultured, together, the corresponding microchannels and static cell culture chamber wells provide an environment in which vascularized hepatic microtissues can be generated. The generated vascularized hepatic microtissue comprises endothelium, which a user can subject to physiological shear stresses by flowing media through the assembled device. In one embodiment, primary human cells are seeded into the cell culture layers. In this embodiment, a human-like vascularized liver tissue system can be generated. Such a system may, for example, be suitable for pharmacokinetic/ADME-Tox assays that can be implemented in the hit-to-lead and lead optimization steps of the drug development process for toxicity and metabolism assessment.

Blood-brain-barrier Model System

For example, in one embodiment, the device provided herein is used to culture one or more cells relevant to a blood-brain-barrier (BBB) model system. In a preferred embodiment, the device suitable for use in the BBB model system comprises at least five layers: (from top to bottom) a well block top, a well block bottom, a first cell culture layer (e.g., a layer comprising porous flow chambers), a second cell culture layer (e.g., a layer comprising static chambers), and a base block. Optionally, the device may further comprise a collection chamber layer. Optionally, the porous membrane of the first cell culture layer comprises electrodes.

For example, in one embodiment, brain microvascular endothelial cells are seeded in the microchannels in the first cell culture layer, for example, onto a bottom surface of the microchannels. Preferably, the bottom surface of the microchannels (i.e., the porous membrane) is coated with one or more extra cellular matrix proteins. Natural (e.g., collagen I) or synthetic (e.g., polyethylene glycol) hydrogels embedded with astrocytes are polymerized directly inside the static cell culture chamber wells of the second cell culture layer. Optionally, other cells of interest (e.g., neurons and/or other glial cells) may be added to one or more of the static cell culture chamber wells. When the seeded first and second cell culture layers are coupled and cultured, the corresponding microchannels and static cell culture chamber wells together provide an environment in which vascularized brain microtissues can be generated. The generated vascularized brain microtissue comprises endothelium, which a user can subject to physiological shear stresses by flowing media through the assembled device. In one embodiment, primary human cells are seeded into the cell culture layers. In this embodiment, a human-like blood-brain-barrier can be generated. Such a system may, for example, be suitable for screening drug candidates and/or drug delivery vehicles. Such a system may, for example, be suitable for investigating BBB-related biological mechanisms.

In various embodiments, a porous membrane comprising electrodes suitable for culture of cells thereon is provided in a device suitable for BBB modeling. A device comprising electrodes may be used, for example to measure one or more of: endothelial barrier function, endothelial ion channel activities, endothelial ligand binding and cell signaling, endothelial cell metabolism, endothelial cytotoxicity, adhesion of circulating cells to the endothelium, transendothelial migration of cells (such as immune cells, metastatic cells, circulating stem cells, pathogens, etc.), and transport of drugs and drug delivery vehicles across the endothelium.

Cell Perfusion Model System

In another example, in one embodiment, the device provided herein is used to assess and/or monitor fluid and/or nutrient exchange in a cell perfusion system. In one embodiment, the device suitable for use in the cell perfusion model system comprises at least four layers: (from top to bottom) a well block top, a well block bottom, a first cell culture layer (e.g., a layer comprising porous flow chambers), and a base block. In one embodiment, the device may further comprise a second cell culture layer (e.g., a layer comprising static chambers). In one embodiment, the device may further comprise a collection chamber layer.

For example, in one embodiment, the microchannels in the first cell culture layer are not seeded with cells. Preferably, the bottom surface of the microchannels (i.e., the porous membrane) is not coated with one or more extra cellular matrix proteins. The static cell culture chamber wells of the second cell culture layer are seeded with cells, such as, for example, cells grown in 3D biomaterials, micromass cultures, embryoid bodies, microtissue constructs, etc. Optionally, other cells of interest may be added to one or more of the static cell culture chamber wells. Optionally, configuration of the static cell culture chamber wells can be designed to house specific cell cultures.

In one embodiment, a perfusion model system comprising cells cultured in a device provided herein may improve cell growth and/or health by exchanging the cell culture medium continuously, thereby delivery fresh nutrients and washing away waste products continuously in contrast to standard tissue culture in which the medium is changed periodically (e.g., every other day). For example, a user may set up a cell culture in the device provided herein to perfuse for a period of time, spent medium being exchanged for fresh medium periodically.

Bacterial Vascular Dissemination Model System

For example, in one embodiment, the device provided herein is used to culture one or more cells relevant to a bacterial vascular dissemination model system. In a preferred embodiment, the device is suitable for use in a Lyme disease model system, the device comprising at least five layers: (from top to bottom) a well block top, a well block bottom, a first cell culture layer (e.g., a layer comprising porous flow chambers), a second cell culture layer (e.g., a layer comprising static chambers), and a base block. Optionally, the device may further comprise a collection chamber layer. Optionally, the porous membrane of the first cell culture layer comprises electrodes. Optionally, the first cell culture layer may comprise a porous membrane comprising electrodes suitable for culture of cells thereon. A device comprising electrodes may be used, for example to measure one or more of: endothelial barrier function, endothelial ion channel activities, endothelial ligand binding and cell signaling, endothelial cell metabolism, endothelial cytotoxicity, adhesion of circulating cells to the endothelium, transendothelial migration of cells (such as immune cells, metastatic cells, circulating stem cells, pathogens, etc.), and transport of drugs and drug delivery vehicles across the endothelium.

For example, in one embodiment, endothelial cells from a tissue of interest such as, for example, post-capillary venules, are seeded in the microchannels in the first cell culture layer, for example, onto a bottom surface of the microchannels. Preferably, the bottom surface of the microchannels (i.e., the porous membrane) is coated with one or more extra cellular matrix proteins. In one embodiment, the static cell culture chamber wells of the second cell culture layer are provided with cell culture media, the cell culture media comprising or lacking a bacterial chemokine. In one embodiment, the static cell culture chamber wells of the second cell culture layer are seeded with cells of interest, the cells being embedded in a hydrogel. When the first and second cell culture layers are coupled and cultured, the corresponding microchannels and static cell culture chamber wells together provide an environment in which bacterial dissemination from blood into tissues can be assayed. A user can load bacteria in cell culture media, which may be flowed through the microchannels of the first cell culture layer, thereby allowing the bacteria to interact with the endothelium grown on the bottom surface of the microchannels, and facilitating extravasation of the bacteria through the endothelial monolayer, through the porous membrane and into the static cell culture chamber wells of the device.

It is contemplated that vascular dissemination of various microorganisms may be studied using one or more embodiments of the device provided herein.

Extravasation and Blood-Subendothelial Transport Model System

The embodiment in which the device is used to provide a Lyme disease model system is one example of a way in which the device may be used to study extravasation and transport from the blood to the subendothelial space. In various embodiments, the device provided herein may be used to model extravasation and transport from the blood to the subendothelial space such as, for example, immune cell trafficking, metastasis, transport of drugs or other compounds, nanoparticle transport, etc.

In one embodiment, a method of performing studies of the effects of drugs, toxins or other chemical agents on the cultured cells. For example, testing of the toxicity of chemical compositions, drugs and other compounds of interest may be examined using the microfluidic device provided herein.

In one embodiment, methods provided herein may comprise a step of imaging cells in the microfluidic device. For example, in embodiments wherein the device comprises an imaging base block, one or more well of the device may be imaged from below or above the base block using imaging equipment known in the art (e.g., a microplate reader). In embodiments wherein the device comprises a imaging base block (i.e., a base block configured for flow), one or more well of the device may be imaged if the imaging base block is replaced with an imaging base block. In this embodiment, cells subjected to a flow based assay using the microfluidic device provided herein may be imaged at one or more time points during the assay by draining the fluid from the device, replacing the imaging base block with an imaging base block, and imaging one or more wells of the device as described above.

Although the invention has been described with reference to certain specific embodiments, various modifications thereof will be apparent to those skilled in the art without departing from the purpose and scope of the invention as outlined in the claims appended hereto. Any examples provided herein are included solely for the purpose of illustrating the invention and are not intended to limit the invention in any way. Any drawings provided herein are solely for the purpose of illustrating various aspects of the invention and are not intended to be drawn to scale or to limit the invention in any way. The disclosures of all prior art recited herein are incorporated herein by reference as if set forth in their entirety.

We claim:

1. A microfluidic device for assaying cells, the microfluidic device comprising:
   a well block comprising a plurality of microwells;
   a first cell culture layer comprising a plurality of microchannels, each microchannel being aligned with one of the plurality of microwells and being in fluid communication with the aligned microwells; and
   a base block, the base block being in fluid communication with the plurality of microchannels, wherein the first cell culture layer is coupled between the well block and the base block to form a liquid tight seal, thereby allowing fluid communication between the plurality of microwells in the well block, the aligned microchannels in the first cell culture layer and the base block.

2. The microfluidic device of claim 1, wherein the plurality of microchannels have defined geometries that produce one or more desired flow rates through the plurality of microchannels.

3. The microfluidic device of claim 1, wherein an internal bottom surface of each of the plurality of microchannels is integral with the first cell culture layer.

4. The microfluidic device of claim 1, wherein an internal bottom surface of each of the plurality of microchannels comprises a porous or semi-porous membrane that is coupled to the first cell culture layer.

5. The microfluidic device of claim 4, wherein the porous or semi-porous membrane comprises electrodes.

6. The microfluidic device of claim 1, further comprising a second cell culture layer comprising a plurality of cell culture chamber wells and corresponding outlets, each cell culture chamber well being aligned with one of the plurality of microchannels and being in fluid communication with the aligned microchannels, each corresponding outlet being in fluid communication with the aligned microchannels and the base block.

7. The microfluidic device of claim 6, wherein the second cell culture layer is coupled between the first cell culture layer and the base block to form a liquid tight seal, thereby allowing fluid communication between each of the plurality of microwells in the well block, the aligned microchannels in the first cell culture layer, the second cell culture layer and the base block.

8. The microfluidic device of claim 6, further comprising a non-permeable layer disposed between the plurality of cell culture chamber wells and the first cell culture layer, wherein the non-permeable layer is for preventing fluid flow in the plurality of cell culture chamber wells.

9. The microfluidic device of claim 1, further comprising a fluid collection layer comprising a plurality of fluid collection chambers, each fluid collection chamber being aligned with and in fluid communication with one of the plurality of microwells and one of the plurality of microchannels, wherein the fluid collection layer is coupled between the well block and the base block to form a liquid tight seal.

10. The microfluidic device of claim 1, wherein the base block comprises an outlet configured to be coupled to a flow or vacuum manifold.

11. A kit for assembling a microfluidic device for assaying cells, the kit comprising:
    at least one well block comprising a plurality of microwells;
    at least one cell culture layer, the at least one cell culture layer comprising:
       a plurality of microchannels, each microchannel being alignable with one of the plurality of microwells and being configured for fluid communication with the alignable microwells; or
       a plurality of cell culture chamber wells, each cell culture chamber well being alignable with one of the plurality of microwells and being configured for fluid communication with the alignable microwells, and a plurality of outlets, each of the plurality of outlets corresponding to one of the plurality of cell culture chamber wells;
    at least one base block for providing a base for the device; and
    at least two seals for forming a seal between the well block and the at least one cell culture layer and the at least one cell culture layer and the base block, wherein upon assembly the at least one cell culture layer may be coupled between the well block and the base block to form a liquid tight seal, thereby allowing fluid communication between each of the plurality of microwells in the well block and the at least one cell culture layer.

12. The kit of claim 11, wherein each of the plurality of microchannels comprises an internal bottom surface comprising a porous or semi-porous membrane that is coupled to the first cell culture layer, the porous or semi-porous membrane being suitable for culturing cells thereon.

13. The kit of claim 12, wherein the porous or semi-porous membrane comprises electrodes.

14. The kit of claim 11, wherein the at least one well block is one or more of a deep well block, wherein the plurality of microwells have a liquid capacity of about 1.5mL, a shallow well block, wherein the plurality of microwells have a liquid capacity of about 0.25mL, or a pool well block comprising a tray having a liquid capacity of about 150 mL, the tray being disposed above and in fluid communication with the plurality of microwells.

15. The kit of claim 11, wherein the at least one cell culture layer comprises at least two cell culture layers.

16. The kit of claim 11, wherein the at least one base block is one or more of:

a base block configured for fluid communication with the cell culture layer and comprises an outlet configured for fluid communication with a flow or vacuum manifold; and a base block configured to allow optical access to the at least one cell culture layer.

17. The kit of claim 11, further comprising:

a fluid collection layer comprising a plurality of fluid collection chambers, each fluid collection chamber being configured for alignment and fluid communication with one of the microwells and one of the microchannels when the well block, first cell culture layer and fluid collection layers are aligned and coupled.

18. The microfluidic device of claim 1, wherein the device may be disassembled by uncoupling the well block, the first cell culture layer and the base block.

* * * * *

UNITED STATES PATENT AND TRADEMARK OFFICE
CERTIFICATE OF CORRECTION

PATENT NO. : 10,481,150 B2
APPLICATION NO. : 15/521744
DATED : November 19, 2019
INVENTOR(S) : Craig Simmons et al.

Page 1 of 1

It is certified that error appears in the above-identified patent and that said Letters Patent is hereby corrected as shown below:

In the Specification

Column 11, Line 15, "(2000," should be --(200f)--.

Column 11, Line 16, "(2000," should be --(200f)--.

Signed and Sealed this
Twenty-eighth Day of January, 2020

Andrei Iancu
*Director of the United States Patent and Trademark Office*